United States Patent
Das et al.

(10) Patent No.: US 9,834,757 B2
(45) Date of Patent: Dec. 5, 2017

(54) HAND, FOOT, AND MOUTH VACCINES AND METHODS OF MANUFACTURE AND USE THEREOF

(71) Applicant: Takeda Vaccines, Inc., Bozeman, MT (US)

(72) Inventors: Subash Chandra Das, Middleton, WI (US); Joseph David Santangelo, Helios (SG); Dan Thomas Stinchcomb, Fort Collins, CO (US); Jorge E. Osorio, Mount Horeb, WI (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

(21) Appl. No.: 14/935,227

(22) Filed: Nov. 6, 2015

(65) Prior Publication Data

US 2016/0129104 A1 May 12, 2016

Related U.S. Application Data

(60) Provisional application No. 62/077,146, filed on Nov. 7, 2014.

(51) Int. Cl.
| | | |
|---|---|---|
| A61K 39/135 | (2006.01) | |
| C12N 7/00 | (2006.01) | |
| A61K 39/12 | (2006.01) | |
| C07K 16/10 | (2006.01) | |
| A61K 39/00 | (2006.01) | |

(52) U.S. Cl.
CPC ............... *C12N 7/00* (2013.01); *A61K 39/12* (2013.01); *C07K 16/1009* (2013.01); *A61K 2039/5252* (2013.01); *A61K 2039/55505* (2013.01); *C07K 2317/33* (2013.01); *C07K 2317/35* (2013.01); *C12N 2770/32334* (2013.01); *C12N 2770/32363* (2013.01)

(58) Field of Classification Search
None
See application file for complete search history.

(56) References Cited

PUBLICATIONS

Premanand et al. (Antiviral Research. 2012; 95: 311-315).*
Lin et al. (Vaccine. 2002; 20: 2485-2493).*
Eckels et al. (Applied Microbiology. 1970; 19 (2): 321-325).*
Huang et al., "Neurologic Complications in Children with Enterovirus 71 Infection", The New England Journal of Medicine, vol. 341, Sep. 23, 1999, pp. 936-942.
Chang et al., "Fulminant Neurogenic Pulmonary Oedema with Hand, Foot, and Mouth Disease", Lancet, vol. 352, Aug. 1, 1998, pp. 367-368.
Ooi et al., "Identification and Validation of Conical Predictors for the Risk of Neurological Involvement in Children with Hand, Foot, and Mouth Disease", BMC Infectious Diseases, vol. 9, No. 3, Jan. 19, 2009, pp. 1-12.
Solomon et al., "Virology, Epidemiology, Pathogenesis, and Control of Enterovirus 71", Lancet Infect Dis, vol. 10, Nov. 2010, pp. 778-790.
McMinn, Peter C., "An Overview of the Evolution of Enterovirus 71 and its Clinical and Public Health Significance", FEMS Microbiology Reviews, vol. 26, 2002, pp. 91-107.
WHO., "WPRO Hand, Foot, and Mouth Disease Situation Update, May 15, 2012", Western Pacific Regional Office of the World Health Organization, pp. 1-4.
Updates on HFMD Situation in Singapore. Hand, Foot & Mouth Disease: Updates: Singapore Ministry of Health, 2012, May 23, 2012.
Pallansch et al., "Enteroviruses: polioviruses, coxsackieviruses, and newer enteroviruses", Fields Virology, 2007, pp. 839-894.
Nagata et al., "Pyramidal and Extrapyramidal Involvement in Experimental Infection of Cynomolgus Monkeys with Enterovirus 71", Journal of Medical Virology, vol. 67, 2002, pp. 207-216.
Yamayoshi et al, "Scavenger Receptor B2 is a Cellular Receptor for Enterovirus 71", Nature Medicine, vol. 15, No. 7, Jul. 2009, pp. 798-801.
Nishimura et al., "Human P-Selectin Glycoprotein Ligand -1 is a Functional Receptor for Enterovirus 71", Nature Medicine, vol. 15, No. 7, Jul. 2009, pp. 794-797.
Oberste et al., "Typing of Human Enteroviruses by Partial Sequencing of VP1", Journal of Clinical Microbiology, vol. 37, May 1999, pp. 1288-1293.
Lee et al., "Challenges to Licensure of Enterovirus 71 Vaccines", PLOS Neglected Tropical Diseases, vol. 6, Issue 8, e1737, Aug. 2012, pp. 1-7.
Brown et al., "Molecular Epidemiology and Evolution of Enterovirus 71 Strains Isolated from 1970 to 1998", Journal of Virology, vol. 73, No. 12, Dec. 1999, pp. 9969-9975.
Chan et al., "Phylogenetic Designation of Enterovirus 71 Genotypes and Subgenotypes using Complete Genome Sequences", Infection, Genetics and Evolution, vol. 10, No. 3, 2010, pp. 404-412.
Yoke-Fun et al., "Phylogenetic Evidence for Inter-typic Recombination in the Emergence of Human Enterovirus 71 Subgenotypes", BMC Microbiology, vol. 6, No. 74, Aug. 30, 2006, pp. 1-11.
Wang et al., "Clinical Spectrum of Enterovirus 71 Infection in Children in Southern Taiwan, with an Emphasis on Neurological Complications", Clinical Infectious Diseases, vol. 29, 1999, pp. 184-190.
Ong et al., "Formaldehyde-inactivated Whole-Virus Vaccine Protects a Murine Model of Enterovirus 71 Encephalomyelitis against Disease", Journal of Virology, vol. 84, No. 1, Jan. 2010, pp. 661-665.
Chong et al., "Production of EV71 vaccine candidates", Human Vaccines & Immunotherapeutics, vol. 8, No. 12, Dec. 2012, pp. 1775-1783.

(Continued)

*Primary Examiner* — Shanon A Foley
(74) *Attorney, Agent, or Firm* — Morrison & Foerster LLP

(57) ABSTRACT

The present disclosure relates to hand, foot, and mouth disease vaccines and immunogenic compositions having one or more antigens from at least one virus that causes hand, foot, and mouth disease in humans, and methods of manufacture, formulation, and testing, and uses thereof.

Figure 1:
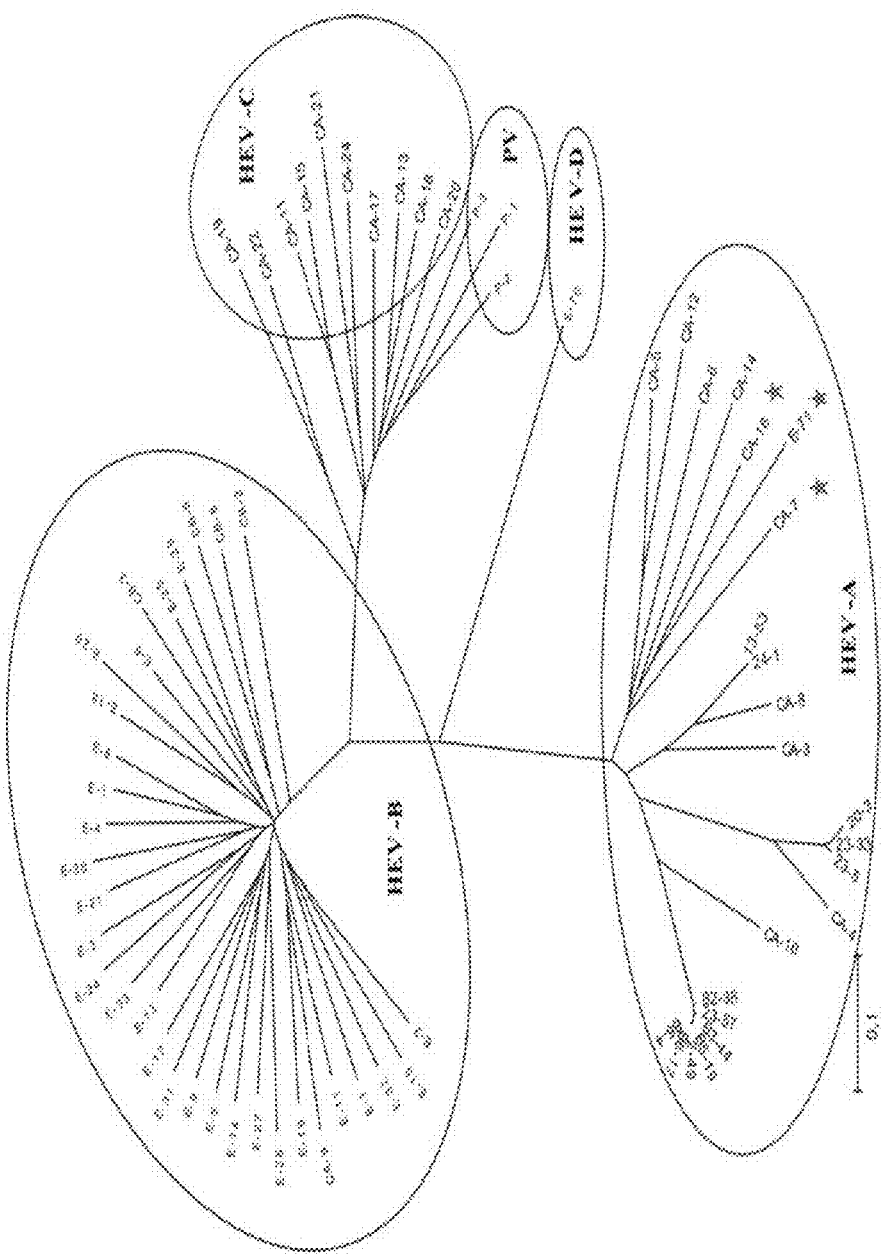

20 Claims, 15 Drawing Sheets
(10 of 15 Drawing Sheet(s) Filed in Color)

(56) References Cited

PUBLICATIONS

Chen et al., "Oral Immunization of Mice using Transgenic Tomato Fruit Expressing VP1 Protein from Enterovirus 71", Vaccine, vol. 24, 2006. pp. 2944-2951.

Meng et al., "Display of VP1 on the Surface of Baculovirus and its Immunogenicity against Heterologous Human Enterovirus 71 Strains in Mice", PLoS ONE, vol. 6, Issue 7, e21757, Jul. 2011, pp. 1-12.

Liu et al., "Combined Peptides of Human Enterovirus 71 Protect against Virus Infection in Mice", Vaccine, vol. 28, 2010, pp. 7444-7451.

Chiu et al., "Protection of neonatal mice from lethal enterovirus 71 infection by maternal immunization with attenuated *Salmonella enterica* Serovar *typhimurium* expressing VP1 of enterovirus 71", Microbes Infect, vol. 8, pp. 1671-1678.

Tung et al., "DNA Vaccine Constructs against Enterovirus 71 Elicit Immune Response in Mice", Genetic Vaccines and Therapy, vol. 5, No. 6, Apr. 19, 2007, pp. 1-13.

Chung et al., "Immunization with Virus-like Particles of Enterovirus 71 Elicits Potent Immune Responses and Protects Mice against Lethal Challenge", Vaccine, vol. 26, Issue 15, 2008, pp. 1855-1862.

Arita et al., "An Attenuated Strain of Enterovirus 71 Belonging to Genotype A Showed a Broad Spectrum of Antigenicity with Attenuated Neurovirulence in Cynomolgus Monkeys", Journal of Virology, vol. 81, No. 17, Sep. 2007, pp. 9386-9395.

Mao et al., "Comparative Analysis of the Immunogenicity and Protective Effects of Inactivated EV71 Vaccines in Mice", PLoS ONE, vol. 7, Issue 9, Sep. 18, 2012, pp. 1-9.

Chou et al., "Immunological Evaluation and Comparison of Different EV71 Vaccine Candidates", Clinical and Developmental Immunology, vol. 2012, Article 831282, 2012, pp. 1-8.

Li et al., "Safety and Immunogenicity of a Novel Human Enterovirus 71 (EV71) Vaccine: a Randomized, Placebo-Controlled, Double-blind, Phase I Clinical Trial", Vaccine, vol. 30, Issue 22, May 9, 2012, pp. 3295-3303.

Zhu et al., "Efficacy, Safety, and Immunology of an Inactivated Alum-adjuvant Enterovirus 71 Vaccine in Children in China: a Multicentre, Randomised, Double-blind, Placebo-controlled, Phase 3 Trial", Lancet, vol. 381, Jun. 8, 2013, pp. 2024-2032.

Cheng et al., "A Phase I, Randomized, Open-label Study to Evaluate the Safety and Immunogenicity of an Enterovirus 71 Vaccine", Vaccine, vol. 31, 2013, pp. 2471-2476.

Bahnemann, Hans G., "Inactivation of Viral Antigens for Vaccine Preparation with Particular Reference to the Application of Binary Ethylenimine", Vaccine, vol. 8, Aug. 1990, pp. 299-303.

Yu et al., "Neutralizing Antibody Provided Protection against Enterovirus Type 71 Lethal Challenge in Neonatal Mice", Journal of Biomedical Science, vol. 7, No. 6, 2000, pp. 523-528.

Liu et al., "Purification and Characterization of Enterovirus 71 Viral Particles Produced from Vero Cells Grown in a Serum-Free Microcarrier Bioreactor System", PLoS One, vol. 6, Issue 5, 2011, pp. 1-9.

Shingler et al., "The Enterovirus 71 A-particle Forms a Gateway to Allow Genome Release: A CryoEM Study of Picornavirus Uncoating", PLoS Pathogens, vol. 9, Issue 3, Mar. 21, 2013, pp. 1-10.

Curry at el., "The Poliovirus 135S Particle is Infectious", Journal of Virology, vol. 70, Oct. 1996, pp. 7125-7131.

Verdier François., "Non-clinical vaccine safety assessment", Toxicology, vol. 174, pp. 37-43.

Verdier et al., "Aluminium Assay and Evaluation of the Local Reaction at Several Time Points after Intramuscular Administration of Aluminium Containing Vaccines in the Cynomolgus Monkey", Vaccine, vol. 23, Issue 11, pp. 1359-1367.

Wang et al., "A Mouse-Adapted Enterovirus 71 Strain Causes Neurological Disease in Mice after Oral Infection", Journal of Virology, vol. 78, Aug. 2004, pp. 7916-7924.

Wang et al., "A mouse muscle-adapted enterovirus 71 strain with increased virulence in mice", Microbes and Infection, vol. 13, Issue 10, Sep. 2011, pp. 862-870.

Huang et al., "Mutations in VP2 and VP1 Capsid Proteins Increase Infectivity and Mouse Lethality of Enterovirus 71 by Vir

FIG. 12

FIG. 14

Percent survival vs. Days Post Challenge

- EV71:CVA16:CVA6 (6/6)
- CVA6 (6/6)
- Normal Mouse Serum (1/6)

FIG. 15

▲ EV71:CVA16:CVA6 (6/6)
● CVA6 (6/6)
■ Normal Mouse Serum (1/6)

Days Post Challenge

TCID50/ml Equivalents (Log10)

SEQUENCE LISTING

<160> NUMBER OF SEQ ID NOS: 5

<210> SEQ ID NO 1
<211> LENGTH: 20
<212> TYPE: DNA
<213> ORGANISM: unknown

```
<220> FEATURE:
<223> OTHER INFORMATION: Synthetic construct

<400> SEQUENCE: 1
tccatgacgt tcctgacgtt                                              20

<210> SEQ ID NO 2
<211> LENGTH: 18
<212> TYPE: DNA
<213> ORGANISM: unknown
<220> FEATURE:
<223> OTHER INFORMATION: Synthetic construct

<400> SEQUENCE: 2
tctcccagcg tgcgccat                                                18

<210> SEQ ID NO 3
<211> LENGTH: 30
<212> TYPE: DNA
<213> ORGANISM: unknown
<220> FEATURE:
<223> OTHER INFORMATION: Synthetic construct

<400> SEQUENCE: 3
accgatgacg tcgccggtga cggcaccacg                                   30

<210> SEQ ID NO 4
<211> LENGTH: 24
<212> TYPE: DNA
<213> ORGANISM: unknown
<220> FEATURE:
<223> OTHER INFORMATION: Synthetic construct

<400> SEQUENCE: 4
tcgtcgtttt gtcgttttgt cgtt                                         24

<210> SEQ ID NO 5
<211> LENGTH: 20
<212> TYPE: DNA
<213> ORGANISM: unknown
<220> FEATURE:
<223> OTHER INFORMATION: Synthetic construct

<400> SEQUENCE: 5
tccatgacgt tcctgatgct                                              20
```

HAND, FOOT, AND MOUTH VACCINES AND METHODS OF MANUFACTURE AND USE THEREOF

CROSS-REFERENCE TO RELATED APPLICATIONS

This application claims the benefit of U.S. Provisional Application No. 62/077,146, filed Nov. 7, 2014, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 606772001000SEQLIST.TXT, date recorded: Oct. 29, 2015, size: 2 KB).

FIELD

The present disclosure relates to hand, foot, and mouth disease vaccines and immunogenic compositions having one or more antigens from at least one virus that causes hand, foot, and mouth disease in humans, and methods of manufacture, formulation, and testing, and uses thereof.

BACKGROUND

Hand, foot, and mouth disease (HFMD) is caused by several members of the human enterovirus A (HEV-A) group. It is generally a self-limiting infection affecting mostly children and is characterized by ulcers and vesicles on the hands, feet and oral cavity. However, a more severe form of disease may occur with neurological symptoms such as meningitis, encephalitis, polio-like paralysis, and brain stem encephalitis leading to pulmonary edema and death (Huang, C C et al., (1999) *N Engl J Med* 341: 936-942; Chang, L Y et al., (1998) *Lancet* 352: 367-368; and Ooi, M H et al., (2009) *BMC Infect Dis* 9: 3). Since the mid-1990s, HFMD infections caused by human enterovirus 71 (EV71) have resulted in significant morbidity and mortality, particularly in the Asia-Pacific region (Solomon, T et al., (2010) *Lancet Infect Dis* 10(11):778-90; and McMinn, PC (2002) *FEMS Microbiol Rev* 26: 91-107). China, Viet Nam, and Singapore reported increased activity in January-May 2012 compared to the same period in 2011. Hand, Foot, and Mouth Disease outbreaks disrupt education and economic activities due to school and childcare center closures in efforts to control disease transmission.

Human enterovirus A belongs to the Picornaviridae family of non-enveloped, positive-sense RNA viruses, which also includes polioviruses and rhinoviruses. Members of the HEV-A group which cause HFMD include Enterovirus 71(EV71) and Coxsackieviruses, including serotypes A1, A4, A6, A10, and A16 (Pallansch and Roos, (2007) Knipe D M, Howley P M, Griffin D E, editors. Fields Virology. Philadelphia, Pa. Lippincott Williams & Wilkins. pp. 839-894; and Kobayashi M et al., *Jpn J Infect Dis* 2013; 66:260-1). HFMD outbreaks due to EV71 infection have the greatest propensity to cause severe neurological disease. Experimental infection of cynomolgus macaques showed that strains isolated across several decades were all neurotropic, as well as showing a broader tissue tropism than polioviruses (Nagata, N et al., (2002) *J Med Virol* 67: 207-216).

EV71 has four capsid proteins (VP1-VP4) and seven nonstructural proteins. In addition to protecting the viral RNA, the capsid proteins recognize receptors on the surface of host cells and contribute to the antigenic profile of the virus (Pallansch and Roos, (2007) Knipe D M, Howley P M, Griffin D E, editors. Fields Virology. Philadelphia, Pa. Lippincott Williams & Wilkins. pp. 839-894). Known human cell surface receptors for EV71 are the scavenger receptor B2 (SCARB2), and the P-selectin glycoprotein ligand 1 (PSGL-1) (Yamayoshi, S et al., (2009) *Nat Med* 15:798-801; and Nishimura, Y et al., (2009) *Nat Med* 15: 794-797).

Although the classical method of typing enteroviruses by serum neutralization defines EV71 as a single serotype [12], current molecular typing methods indicate that several genogroups have been circulating in the Asia-Pacific region at least since the 1990s (Lee, M S et al., (2012) *PLoS Negl Trop Dis* 6: e1737). EV71 isolates were previously classified into genogroups A, B, and C and sub-genogroups based on VP1 nucleotide sequences alone (Brown, B A et al., (1999) *J Virol* 73: 9969-9975); nucleotide sequence identity of the VP1 gene is >92% within genogroups, whereas nucleotide sequence identity between the genogroups is 78-83% (Solomon, T et al., (2010) *Lancet Infect Dis* 10(11):778-90). However, whole-genome sequencing resulted in the reclassification of subgenogroup B5 under B4 and addition of genogroup D; the authors suggested that the 3D polymerase sequence together with VP1 better represented whole genomes (Chan, Y F et al., (2009) *Infect Genet Evol* 10(3): 404-12). Recombination between genogroups and with other Human enterovirus A serotypes also occurs (Yoke-Fun and AbuBakar (2006) *BMC Microbiol* 6: 74).

At present no specific antiviral therapy or vaccine against EV71 is available. Intravenous immunoglobulin has been used in severe HFMD cases, with some therapeutic benefit suggested by the outcomes but as yet unproven by clinical trials (Ooi, M H et al., (2009) *BMC Infect Dis* 9: 3; and Wang, S M et al., (1999) *Clin Infect Dis* 29: 184-190). Preventive and control measures during EV71 outbreaks are limited to surveillance, closure of educational and childcare facilities, and isolation of patients.

BRIEF SUMMARY

Thus, there is a need to develop vaccines and immunogenic compositions for treating and/or preventing hand, food, and mouth disease, particularly in children. In order to meet this need, the present disclosure provides vaccines and immunogenic compositions for treating and/or preventing hand, foot, and mouth disease that include antigens from at least one virus that causes hand, foot, and mouth disease in humans, such as EV71. Advantageously, the antigens may include at least one adaptation mutation that allows for production in cultured non-human cell lines such as Vero cells. Moreover, as disclosed herein, the vaccines and immunogenic compositions of the present disclosure have been demonstrated to induce a protective immune response against viruses that cause hand, foot, and mouth disease in humans.

Accordingly, certain aspects of the present disclosure provide a hand, foot, and mouth vaccine containing one or more antigens from at least one inactivated virus that causes hand, foot and mouth disease in humans, where the at least one virus was inactivated with BEI. Other aspects of the present disclosure provide a hand, foot, and mouth immunogenic composition containing one or more antigens from at least one inactivated virus that causes hand, foot and mouth disease in humans, where the at least one virus was inactivated with BEI. Other aspects of the present disclosure provide a method for treating or preventing hand, foot, and mouth disease in a subject in need thereof, by administering to the subject a therapeutically effective amount of any of the vaccines or immunogenic compositions disclosed herein. Other aspects of the present disclosure provide a method for inducing an immune response in a subject in need thereof, by administering to the subject an immunogenic amount of any of the vaccines or immunogenic compositions disclosed herein. Other aspects of the present disclosure provide a method for inactivating a hand, foot, and mouth virus preparation, by: (a) isolating the hand, foot, and mouth virus preparation from one or more non-human cells, where the cells are used to produce the virus preparation; and (b) treating the virus preparation with an effective amount of BEI; and where the virus is selected from one or more of EV71, CA6, and CA16.

Other aspects of the present disclosure provide a hand, foot, and mouth vaccine containing one or more antigens from at least one virus that causes hand, foot and mouth disease in humans and a detergent in an effective concentration. Other aspects of the present disclosure provide a hand, foot, and mouth immunogenic composition containing one or more antigens from at least one virus that causes hand, foot and mouth disease in humans and a detergent in an effective concentration. Other aspects of the present disclosure provide a method for treating or preventing hand, foot, and mouth disease in a subject in need thereof, containing administering to the subject a therapeutically effective amount of any of the vaccines or immunogenic compositions disclosed herein. Other aspects of the present disclosure provide a method for inducing an immune response in a subject in need thereof, containing administering to the subject an immunogenic amount of any of the vaccines or immunogenic compositions disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a tree depicting the phylogenetic relationship of human enteroviruses.

FIG. 2 shows the genetic structure of an exemplary EV71 strain.

FIG. 3 shows SDS-PAGE and Western blot analysis of purified inactivated EV71 antigen.

FIG. 4 shows a transmission electron micrograph of purified inactivated EV71.

FIG. 5 shows the kinetics of serum neutralizing antibody responses to EV71 with or without adjuvant.

FIG. 6 shows a dose titration of EV71 antigen.

FIG. 7 shows the geometric mean titer of antibodies to EV71, CVA16, and CVA6.

FIG. 8 shows the treatment protocol for immunization and challenge with EV71 and CVA16 in mice.

FIG. 9 shows survival rate of mice challenged with EV71.

FIG. 10 shows the serum EV71 viral titer in immunized mice.

FIG. 11 shows survival rate of mice challenged with CVA16.

Figure 12:
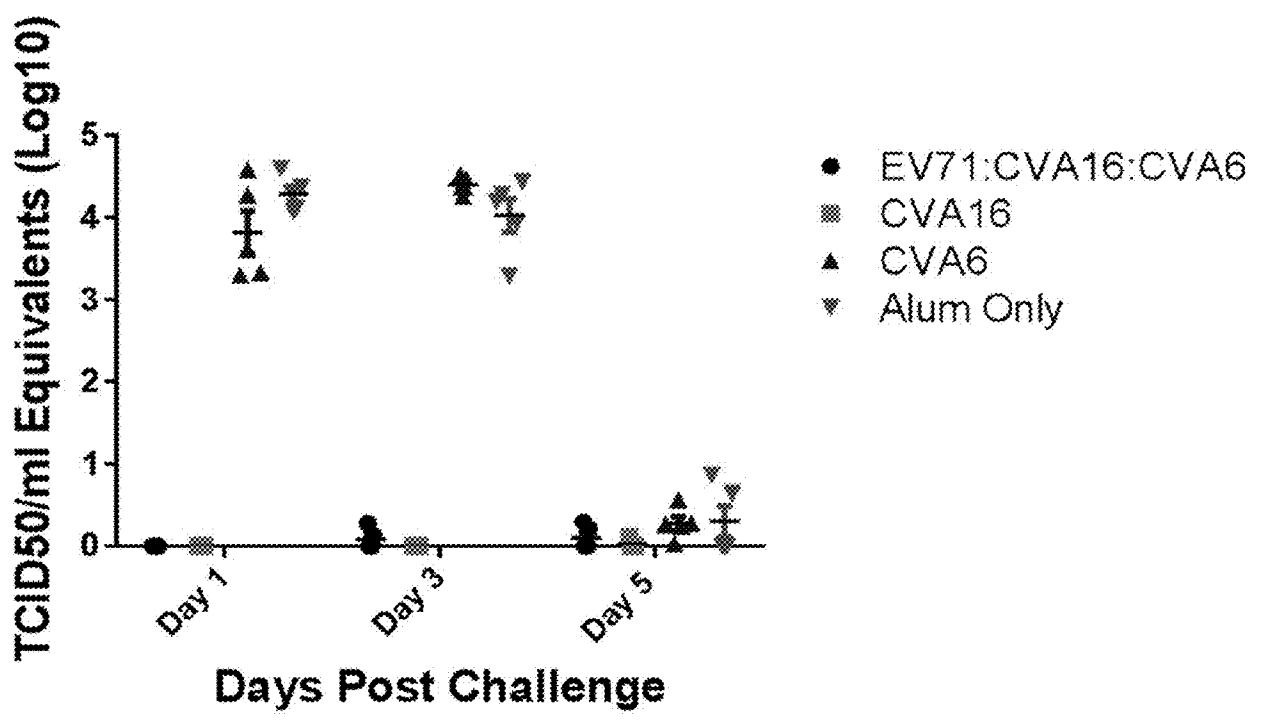

FIG. 12 shows the serum CVA16 viral titer in immunized mice.

FIG. 13 shows the treatment protocol for passive immunization and challenge with CVA6 in mice.

FIG. 14 shows survival rate of mice challenged with CVA6.

FIG. 15 shows the serum CVA6 viral titer in immunized mice.

DETAILED DESCRIPTION

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Hand, Foot, and Mouth Disease Causing Viruses

Certain aspects of the present disclosure relate to at least one virus that causes hand, foot, and mouth disease that may be useful in vaccines and/or immunogenic compositions including, without limitation, purified viruses, inactivated viruses, attenuated viruses, recombinant viruses, or purified and/or recombinant viral proteins for subunit vaccines.

Hand, foot, and mouth disease in humans (HFMD) is caused by several members of the human enterovirus A (HEV-A) group (FIG. 1). Human enterovirus A belongs to the Picornaviridae family of non-enveloped, positive-sense RNA viruses, which also includes polioviruses and rhinoviruses. Members of the HEV-A group that can cause HFMD include Enterovirus 71 (EV71) and Coxsackieviruses. Accordingly, examples of suitable viruses of the present disclosure that cause hand, foot, and mouth disease include, without limitation, Enterovirus 71 (EV71), Coxsackievirus A strains, including serotypes A1, A2, A4, A5, A6, A8, A9, A10, or A16, or Coxsackievirus B strains, including serotype B3 or B5 or any combination thereof. As used herein, the term "CA6" is used interchangeably with "CVA6" and "Coxsackievirus A6". As used herein, the term "CA16" is used interchangeably with "CVA16" and "Coxsackievirus A16". In some embodiments, the at least one virus may be one or more, two or more, or three viruses selected from EV71, CA6, and CA16. In some embodiments, the at least one virus may be EV71 and CA6. In some embodiments, the at least one virus may be EV71 and CA16. In some embodiments, the at least one virus may be CA6 and CA16. In some embodiments, the at least one virus may be EV71.

Accordingly, in some embodiments, viruses of the present disclosure that cause hand, foot, and mouth disease may be used in any of the vaccines and/or immunogenic compositions disclosed herein. For example, viruses of the present disclosure that cause hand, foot, and mouth disease may be used to provide one or more antigens useful for treating or preventing hand, foot, and mouth disease in a subject in need thereof and/or inducing an immune response, such as a protective immune response, against hand, foot, and mouth disease in a subject in need thereof.

Viral Antigens

Other aspects of the present disclosure relate to one or more antigens from at least one virus that causes hand, foot and mouth disease that may be useful in vaccines and/or immunogenic compositions including, without limitation, purified viruses, inactivated viruses, attenuated viruses, recombinant viruses, or purified and/or recombinant viral proteins for subunit vaccines.

Antigens of the present disclosure may be any substance capable of eliciting an immune response. Examples of suitable antigens include, but are not limited to, whole virus, attenuated virus, inactivated virus, proteins, polypeptides (including active proteins and individual polypeptide epitopes within proteins), glycopolypeptides, lipopolypeptides, peptides, polysaccharides, polysaccharide conjugates, peptide and non-peptide mimics of polysaccharides and other molecules, small molecules, lipids, glycolipids, and carbohydrates.

In some embodiments, antigens of the present disclosure may be from any virus known to cause HFMD, including, without limitation, Enterovirus 71(EV71), Coxsackievirus A strains, including serotypes A1, A2, A4, A5, A6, A8, A9, A10, or A16, or Coxsackievirus B strains, including serotype B3 or B5, or any combination thereof. In some embodiments, antigens of the present disclosure may be one or more, two or more, three or more, four or more, five or more, six or more, seven or more, eight or more, nine or more, or ten or more antigens selected from EV71, CA6, and CA16. In some embodiments, antigens of the present disclosure may be from EV71 and CA6. In some embodiments, antigens of the present disclosure may be from EV71 and CA16. In some embodiments, antigens of the present disclosure may be from CA6 and CA16. In some embodiments, antigens of the present disclosure may be from EV71. In some embodiments, antigens of the present disclosure may be from CA6. In some embodiments, antigens of the present disclosure may be from CA16.

Antigens of the present disclosure may include at least one non-human cell adaptation mutation. Adaptation mutations may be generated by adapting a virus to growth in a particular cell line. For example, a cell may be transfected with a virus and passaged such that the virus replicates and its nucleic acid mutates. Nucleic acid mutations may be point mutations, insertion mutations, or deletion mutations. Nucleic acid mutations may lead to amino acid changes within viral proteins that facilitate growth of the virus in a non-human cell. Adaptation mutations may facilitate phenotypic changes in the virus, including altered plaque size, growth kinetics, temperature sensitivity, drug resistance, virulence, and virus yield in cell culture. These adaptive mutations may be useful in vaccine manufacture by increasing the speed and yield of virus cultured in a cell line. In addition, adaptive mutations may enhance immunogenicity of viral antigens by altering the structure of immunogenic epitopes.

Accordingly, in certain embodiments, antigens of the present disclosure from at least one virus that causes hand, foot and mouth disease include at least one non-human cell adaptation mutation. In certain embodiments, the adaptation mutations are mutations of a viral antigen to a non-human cell. In some embodiments, the non-human cell may be a mammalian cell. Examples of non-human mammalian cells include, without limitation, VERO cells (from monkey kidneys), MDBK cells, MDCK cells, ATCC CCL34 MDCK (NBL2) cells, MDCK 33016 (deposit number DSM ACC 2219 as described in WO97/37001) cells, BHK21-F cells, HKCC cells, or Chinese hamster ovary cells (CHO cells). In some embodiments, the non-human cell may be a monkey cell. In some embodiments, the monkey cell is from a Vero cell line. Examples of suitable Vero cell lines include, without limitation, WHO Vero 10-87, ATCC CCL-81, Vero 76 (ATCC Accession No. CRL-1587), or Vero C1008 (ATCC Accession No. CRL-1586).

Figure 2:
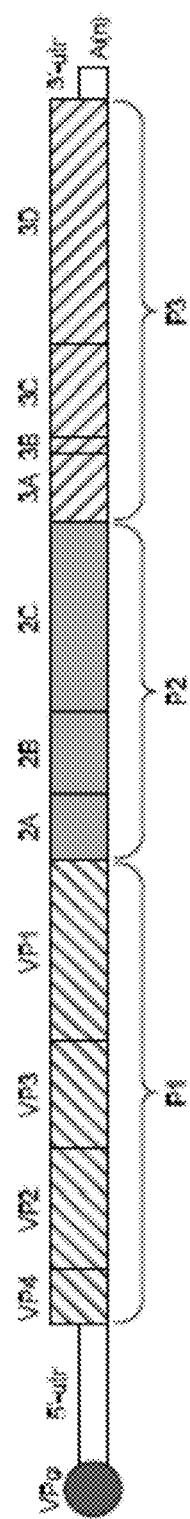
Figure 3:
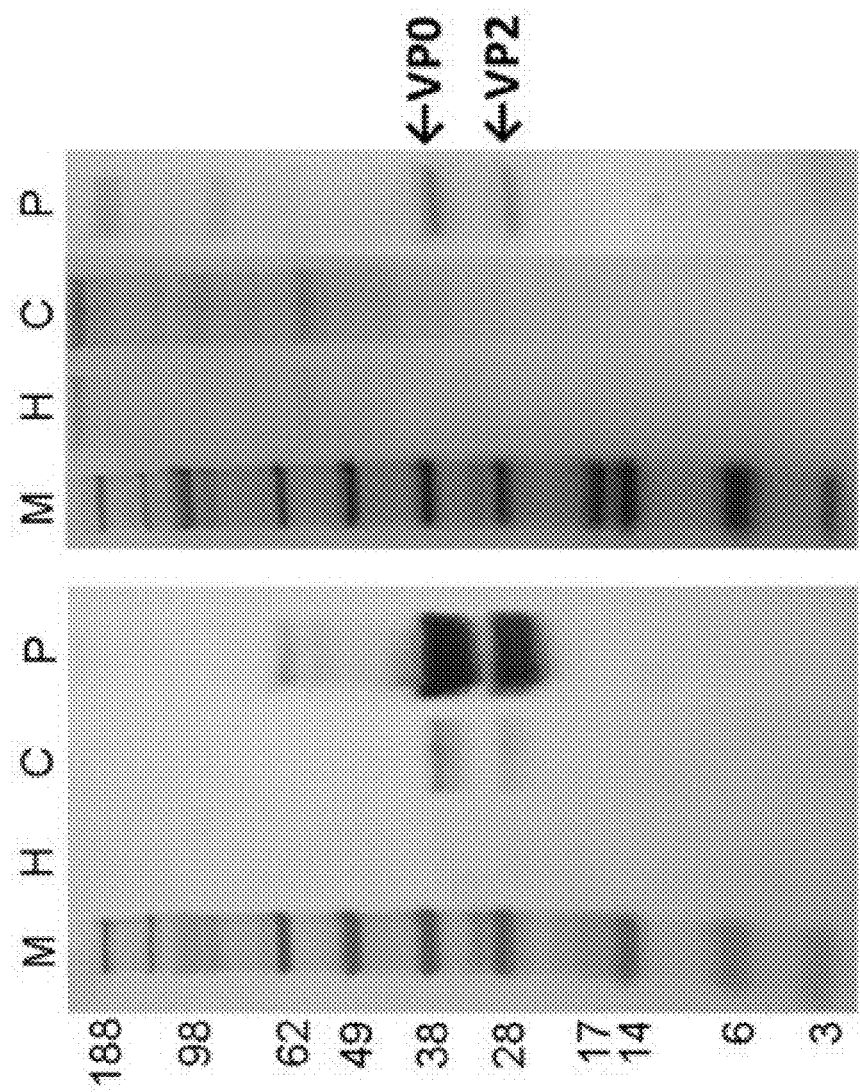
Figure 4:
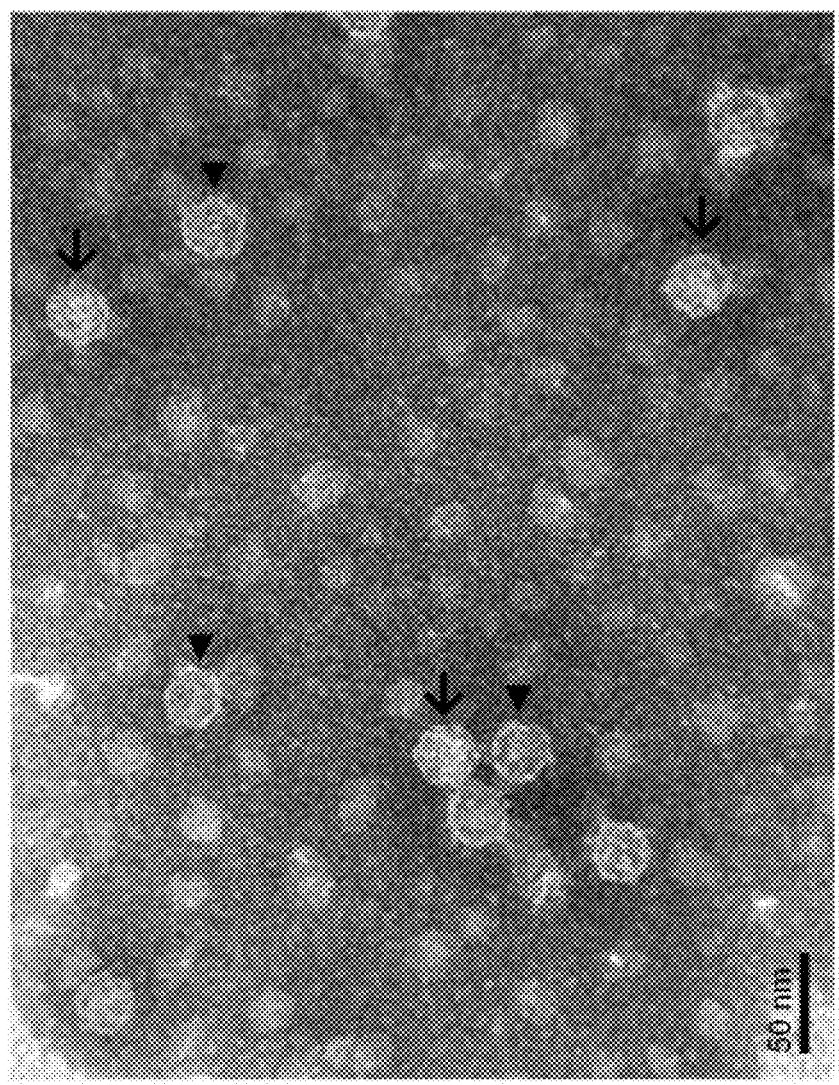

EV71, CA6, and CA16 possess linear, positive sense, single-stranded RNA genomes (FIG. 2). Each of these viral genomes encodes both structural and nonstructural polypeptides. Structural polypeptides encoded by each of these viruses include, without limitation, VP1, VP2, VP3, and VP4, which together may compose the viral capsid. Nonstructural polypeptides encoded by each of these viruses include, without limitation, 2A, 2B, 2C, 3A, 3B, 3C, and 3D, which are involved in, for example, virus replication and virulence.

Accordingly, in certain embodiments, antigens of the present disclosure may contain at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, or more non-human cell adaptation mutations within one or more, two or more, three or more, four or more, five or more, six or more, seven or more, eight or more, nine or more, or ten or more viral antigens, including, without limitation, VP1, VP2, VP3, 2A, 2B, 2C, 3A, 3B, 3C, and 3D. In some embodiments, antigens of the present disclosure include whole, inactivated virus that may contain at least one, at least two, at least three, at least four, at least five, at least six, at least seven, at least eight, at least nine, at least 10, or more non-human cell adaptation mutations within the 5' or 3' untranslated region (UTR) of the virus.

In some embodiments, the one or more antigens include the VP1 polypeptide of EV71, and the at least one non-human cell adaptation mutation is within the VP1 polypeptide. In other embodiments, the one or more antigens include the VP1 polypeptide of CA6, and the at least one non-human cell adaptation mutation is within the VP1 polypeptide. In other embodiments, the one or more antigens include the VP2 polypeptide of CA6, and the at least one non-human cell adaptation mutation is within the VP2 polypeptide. In other embodiments, the one or more antigens include the VP3 polypeptide of CA6, and the at least one non-human cell adaptation mutation is within the VP3 polypeptide. In other embodiments, the one or more antigens include the 2A polypeptide of CA16, and the at least one non-human cell adaptation mutation is within the 2A polypeptide. In other embodiments, the one or more antigens include the VP2 polypeptide of CA16, and the at least one non-human cell adaptation mutation is within the VP2 polypeptide. In other embodiments, the one or more antigens include the VP1 polypeptide of CA16, and the at least one non-human cell adaptation mutation is within the VP1 polypeptide. In some embodiments, antigens of the present disclosure may contain at least one non-human cell adaptation mutation within the 5' untranslated region (UTR) of a virus of the present disclosure, including without limitation, EV71, CA6, and CA16.

In some embodiments, antigens of the present disclosure from at least one virus that causes hand, foot and mouth disease may be used in any of the vaccines and immunogenic compositions of the present disclosure. For example, the antigens of the present disclosure may be useful for treating or preventing hand, foot, and mouth disease in a subject in need thereof and/or inducing an immune response, such as a protective immune response, against hand, foot, and mouth disease in a subject in need thereof.

Production of Vaccines and Immunogenic Compositions

Other aspects of the present disclosure relate to hand, foot, and mouth vaccines and immunogenic compositions containing one or more antigens of the present disclosure from at least one virus that causes hand, foot and mouth disease. Such vaccines and immunogenic compositions may be useful, for example, for treating or preventing hand, foot, and mouth disease in a subject in need thereof and/or inducing an immune response, such as a protective immune response, against hand, foot, and mouth disease in a subject in need thereof. Vaccines and/or immunogenic compositions of the present disclosure may include, without limitation, purified viruses, inactivated viruses, attenuated viruses, recombinant viruses, purified and/or recombinant viral proteins for subunit vaccines. Vaccines and/or immunogenic compositions of the present disclosure may further include a purified antigen vaccine or immunogenic composition, a subunit vaccine or immunogenic composition, an inactivated whole virus vaccine or immunogenic composition, or an attenuated virus vaccine or immunogenic composition.

Production of vaccines and/or immunogenic compositions of the present disclosure includes growth of at least one virus that causes hand, foot, and mouth disease, with antigens being prepared from the grown virus. Growth in cell culture is a method for preparing vaccines and/or immunogenic compositions of the present disclosure. Cells for viral growth may be cultured in suspension or in adherent conditions.

Cell lines suitable for growth of the at least one virus of the present disclosure are preferably of mammalian origin, and include but are not limited to: VERO cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO97/37001), cat, and rodent (e.g. hamster cells such as BHK21-F, HKCC cells, or Chinese hamster ovary cells (CHO cells)), and may be obtained from a wide variety of developmental stages, including for example, adult, neonatal, fetal, and embryo. In certain embodiments, the cells are immortalized (e.g. PERC.6 cells, as described in WO01/38362 and WO02/40665, and as deposited under ECACC deposit number 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal cells (e.g., epithelial, mesangial, proximal tubule), skeletal cells (e.g. chondrocyte, osteoclast, osteoblast), muscle cells (e.g. myoblast, skeletal, smooth, bronchial), liver cells, retinoblasts, and stromal cells. WO97/37000 and WO97/37001 describe production of animal cells and cell lines that capable of growth in suspension and in serum free media and are useful in the production and replication of viruses.

Culture conditions for the above cell types are known and described in a variety of publications, or alternatively culture medium, supplements, and conditions may be purchased commercially, such as for example, as described in the catalog and additional literature of Cambrex Bioproducts (East Rutherford, N.J.).

In certain embodiments, the cells used in the methods described herein are cultured in serum free and/or protein free media. A medium is referred to as a serum-free medium in the context of the present disclosure in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Known serum-free media include Iscove's medium, Ultra-CHO medium (BioWhittaker) or EX-CELL (JRH Bioscience). Ordinary serum-containing media include Eagle's Basal Medium (BME) or Minimum Essential Medium (MEM) (Eagle, Science, 130, 432 (1959)) or Dulbecco's Modified Eagle Medium (DMEM or EDM), which are ordinarily used with up to 10% fetal calf serum or similar additives. Optionally, Minimum Essential Medium (MEM) (Eagle, Science, 130, 432 (1959)) or Dulbecco's Modified Eagle Medium (DMEM or EDM) may be used without any serum containing supplement. Protein-free media like PF-CHO (JHR Bioscience), chemically-defined media like ProCHO 4CDM (BioWhittaker) or SMIF 7 (Gibco/BRL Life Technologies) and mitogenic peptides like Primactone, Pepticase or HyPep™ (all from Quest International) or lactalbumin hydrolyzate (Gibco and other manufacturers) are also adequately known in the prior art. The media additives based on plant hydrolyzates have the special advantage that contamination with viruses, mycoplasma or unknown infectious agents can be ruled out.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or TCID50) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at an m.o.i of about 0.01. Infected cells may be harvested from 30 to 60 hours post infection, or 4 to 10 days post infection. In certain embodiments, the cells are harvested 34 to 48 hours post infection. In certain preferred embodiments, the cells are harvested 4 to 7 hours post infection. More preferably, the cells are harvested 4 to 5 days post infection. In some embodiments, proteases (e.g., trypsin) may be added during cell culture to allow viral release, and the proteases may be added at any suitable stage during the culture. Alternatively, in certain embodiments, the supernatant of infected cell cultures may be harvested and the virus may isolated or otherwise purified from the supernatant.

The viral inoculum and the viral culture are preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [WO2006/027698].

Where virus has been grown on a cell line then it is standard practice to minimize the amount of residual cell line DNA in the final vaccine, in order to minimize any oncogenic activity of the DNA. Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references [Lundblad (2001) Biotechnology and Applied Biochemistry 34:195-197, *Guidance for Industry: Bioanalytical Method Validation*. U.S. Department of Health and Human Services Food and Drug Administration Center for Drug Evaluation and Research (CDER) Center for Veterinary Medicine (CVM). May 2001.] involving a two-step treatment, first using a DNase (e.g. Benzonase), which may be used during viral growth, and then a cationic detergent (e.g. CTAB), which may be used during virion disruption. Removal by β-propiolactone treatment can also be used.

Production of Antigens

Antigens of the present disclosure for use in vaccines and/or immunogenic compositions including, without limitation, purified viruses, inactivated viruses, attenuated viruses, recombinant viruses, or purified and/or recombinant viral proteins for subunit vaccines to treat or prevent hand, foot, and mouth disease and/or induce an immune response, such as a protective immune response, against hand, foot, and mouth disease, may be produced and/or purified or otherwise isolated by any suitable method known in the art. Antigens of the present disclosure may include, without limitation, whole virus, attenuated virus, inactivated virus, proteins, polypeptides (including active proteins and individual polypeptide epitopes within proteins), glycopolypeptides, lipopolypeptides, peptides, polysaccharides, polysaccharide conjugates, peptide and non-peptide mimics of polysaccharides and other molecules, small molecules, lipids, glycolipids, and carbohydrates produced, derived, purified, and/or otherwise isolated from at least one virus that causes hand, foot, and mouth disease. For example, suitable antigens may include, without limitation, structural polypeptides such as VP1, VP2, VP3, and VP4, and non-structural polypeptides, such as 2A, 2B, 2C, 3A, 3B, 3C, and 3D from viruses such as EV71, CA6, and CA16.

Antigen of the present disclosure may be synthesized chemically or enzymatically, produced recombinantly, isolated from a natural source, or a combination of the foregoing. In certain embodiments, antigens of the present disclosure are produced, purified, isolated, and/or derived from at least one virus of the present disclosure that causes hand, foot, and mouth disease, such as EV71, CA6, and CA16. Antigens of the present disclosure may be purified, partially purified, or a crude extract. In some embodiments, antigens of the present disclosure are viruses, such as inactivated viruses, produced as described in the above section entitled "Production of Vaccines and Immunogenic Compositions."

In certain embodiments, one or more antigens of the present disclosure may be produced by culturing a non-human cell. Cell lines suitable for production of the one or more antigens of the present disclosure are preferably of mammalian origin, and include but are not limited to: VERO cells (from monkey kidneys), horse, cow (e.g. MDBK cells), sheep, dog (e.g. MDCK cells from dog kidneys, ATCC CCL34 MDCK (NBL2) or MDCK 33016, deposit number DSM ACC 2219 as described in WO97/37001), cat, and rodent (e.g. hamster cells such as BHK21-F, HKCC cells, or Chinese hamster ovary cells (CHO cells)), and may be obtained from a wide variety of developmental stages, including for example, adult, neonatal, fetal, and embryo. In certain embodiments, the cells are immortalized (e.g. PERC.6 cells, as described in WO01/38362 and WO02/40665, and as deposited under ECACC deposit number 96022940). In preferred embodiments, mammalian cells are utilized, and may be selected from and/or derived from one or more of the following non-limiting cell types: fibroblast cells (e.g. dermal, lung), endothelial cells (e.g. aortic, coronary, pulmonary, vascular, dermal microvascular, umbilical), hepatocytes, keratinocytes, immune cells (e.g. T cell, B cell, macrophage, NK, dendritic), mammary cells (e.g. epithelial), smooth muscle cells (e.g. vascular, aortic, coronary, arterial, uterine, bronchial, cervical, retinal pericytes), melanocytes, neural cells (e.g. astrocytes), prostate cells (e.g. epithelial, smooth muscle), renal cells (e.g. epithelial, mesangial, proximal tubule), skeletal cells (e.g. chondrocyte, osteoclast, osteoblast), muscle cells (e.g. myoblast, skeletal, smooth, bronchial), liver cells, retinoblasts, and stromal cells. WO97/37000 and WO97/37001 describe production of animal cells and cell lines that capable of growth in suspension and in serum free media and are useful in the production of viral antigens. In certain embodiments, the non-human cell is cultured in serum-free media.

Polypeptide antigens may be isolated from natural sources using standard methods of protein purification known in the art, including, but not limited to, liquid chromatography (e.g., high performance liquid chromatography, fast protein liquid chromatography, etc.), size exclusion chromatography, gel electrophoresis (including one-dimensional gel electrophoresis, two-dimensional gel electrophoresis), affinity chromatography, or other purification technique. In many embodiments, the antigen is a purified antigen, e.g., from about 50% to about 75% pure, from about 75% to about 85% pure, from about 85% to about 90% pure, from about 90% to about 95% pure, from about 95% to about 98% pure, from about 98% to about 99% pure, or greater than 99% pure.

One may employ solid phase peptide synthesis techniques, where such techniques are known to those of skill in the art. See Jones, The Chemical Synthesis of Peptides (Clarendon Press, Oxford) (1994). Generally, in such methods a peptide is produced through the sequential additional of activated monomeric units to a solid phase bound growing peptide chain.

Well-established recombinant DNA techniques can be employed for production of polypeptides, where, e.g., an expression construct comprising a nucleotide sequence encoding a polypeptide is introduced into an appropriate host cell (e.g., a eukaryotic host cell grown as a unicellular entity in in vitro cell culture, e.g., a yeast cell, an insect cell, a mammalian cell, etc.) or a prokaryotic cell (e.g., grown in in vitro cell culture), generating a genetically modified host cell; under appropriate culture conditions, the protein is produced by the genetically modified host cell.

Besides killed and attenuated virus immunogenic compositions, one can use a subunit immunogenic composition or other type of immunogenic composition which presents to the animal the antigenic components of hand, foot, and mouth disease virus. The antigenic component may be a protein, glycoprotein, lipid-conjugated protein or glycoprotein, a modified lipid moiety, or other viral component which, when injected into a human, stimulates an immune response in the human such that the human develops protective immunity against hand, foot, and mouth disease. For a subunit immunogenic composition, the virus can be cultured on mammalian cells, as described above. The cell culture can be homogenized and an immunogenic composition can be isolated by passage of the cell culture homogenate over the appropriate column or through the appropriate pore size filter or via centrifugation of the cell culture homogenate.

If the antigenic component is a protein, then one can isolate the nucleic acid which encodes that protein and generate an immunogenic composition that contains that isolated nucleic acid. The nucleic acid encoding the antigenic component can be placed on a plasmid downstream of a signal sequence of a eukaryotic promoter. That plasmid can contain one or more selectable markers and be transfected into an attenuated prokaryotic organism, such as *Salmonella* spp., *Shigella* spp., or other suitable bacteria. The bacteria can then be administered to the human so that the human can generate a protective immune response to the antigenic component. Alternatively, the nucleic acid encoding the antigenic component can be placed downstream of a prokaryotic promoter, have one or more selectable markers, and be transfected into an attenuated prokaryotic organism such as *Salmonella* spp., *Shigella* spp., or other suitable bacteria. The bacteria can then be administered to the eukaryotic subject for which immune response to the antigen of interest is desired. See, for example, U.S. Pat. No. 6,500,419 to Hone, et al.

For a subunit immunogenic composition, the nucleic acid encoding a proteinaceous antigenic component of a hand, foot, and mouth disease virus can be cloned into a plasmid such as those described in International Patent Application Publication Number WO 00/32047 (Galen) and International Patent Application Publication Number WO 02/083890 (Galen). Then the plasmid can be transfected into bacteria and the bacteria can produce the desired antigenic protein. One can isolate and purify the desired antigenic protein by a variety of methods described in both patent applications.

Virus Inactivation

Certain aspects of the present disclosure relate to hand, foot, and mouth vaccines and immunogenic compositions containing one or more antigens from at least one virus that causes hand, foot and mouth disease. Vaccines and/or immunogenic compositions of the present disclosure may include a purified virus, a whole virus, a recombinant virus, a live attenuated whole virus or, preferably, an inactivated whole virus, or subunits, polypeptides, and/or antigens from an inactivated virus. As such, certain embodiments of the present disclosure relate to hand, foot, and mouth vaccines and/or immunogenic compositions containing one or more antigens from at least one inactivated virus that causes hand, foot and mouth disease. Methods of inactivating or killing viruses to destroy their ability to infect mammalian cells are known in the art. Such methods include both chemical and physical means. Suitable means for inactivating a virus include, without limitation, treatment with an effective amount of one or more agents selected from detergents, formalin (also referred to herein as "formaldehyde"), beta-propiolactone (BPL), binary ethylamine (BEI), acetyl ethyleneimine, heat, electromagnetic radiation, x-ray radiation, gamma radiation, ultraviolet radiation (UV radiation), UV-A radiation, UV-B radiation, UV-C radiation, methylene blue, psoralen, carboxyfullerene (C60) and any combination of any thereof.

In certain embodiments of the present disclosure, the at least one virus is chemically inactivated. Agents for chemical inactivation and methods of chemical inactivation are well-known in the art and described herein. In some embodiments, the at least one virus is chemically inactivated with one or more of BPL, formalin, or BEI. In certain embodiments where the at least one virus is chemically inactivated with BPL, the virus may contain one or more modifications. In some embodiments, the one or more modifications may include a modified nucleic acid. In some embodiments, the modified nucleic acid is an alkylated nucleic acid. In other embodiments, the one or more modifications may include a modified polypeptide. In some embodiments, the modified polypeptide contains a modified amino acid residue including one or more of a modified cysteine, methionine, histidine, aspartic acid, glutamic acid, tyrosine, lysine, serine, and threonine. In certain embodiments where the at least one virus is chemically inactivated with formalin, the virus may contain one or more modifications. In some embodiments, the one or more modifications may include a modified polypeptide. In some embodiments, the one or more modifications may include a cross-linked polypeptide. In some embodiments where the at least one virus is chemically inactivated with formalin, the vaccine or immunogenic composition further includes formalin. In certain embodiments of the present disclosure, the at least one virus was inactivated with BEI. In certain embodiments where the at least one virus was inactivated with BEI, the virus contains one or more modifications. In some embodiments, the one or more modifications includes a modified nucleic acid. In some embodiments, the modified nucleic acid is an alkylated nucleic acid.

In some embodiments where the at least one virus is chemically inactivated with BEI or BPL, any residual unreacted BEI or BPL may be neutralized (i.e., hydrolyzed) with sodium thiosulfate. Generally, sodium thiosulfate is added in excess. In some embodiments, sodium thiosulfate may be added at a concentration that ranges from about 25 mM to about 100 mM, from, about 25 mM to about 75 mM, or from about 25 mM to about 50 mM. In certain embodiments, sodium thiosulfate may be added at a concentration of about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, or about 40 mM at a ratio of 1 part concentrated sodium thiosulfate to 20 parts of BEI. In some embodiments, the solutions may be mixed using a mixer, such as an in-line static mixer, and subsequently filtered (e.g., clarified). Generally, the pumping of the two solutions through the mixer results in complete mixing and neutralization of BEI by the sodium thiosulfate.

Certain embodiments of the present disclosure relate to a method for inactivating a hand, foot, and mouth virus preparation. In some embodiments, the method involves (a) isolating the hand, foot, and mouth virus preparation from one or more non-human cells that are used to produce the virus preparation and (b) treating the virus preparation with an effective amount of BEI. In certain embodiments, treating with an effective amount of BEI includes, without limitation, treating with BEI in an amount that ranges from about 0.25% v/v to about 3.0% v/v. In certain embodiments, the isolated and treated virus is selected from one or more of EV71, CA6, and CA16. In certain embodiments of the method, the virus preparation is treated with BEI at a temperature that ranges from about 25° C. to about 42° C. In certain embodiments of the method, the virus preparation is treated with BEI for a period of time that ranges from about 1 hour to about 10 hours. In certain embodiments, the method further involves inactivating (i.e., hydrolyzing) unreacted BEI with an effective amount of sodium thiosulfate. In some embodiments, the effective amount of sodium thiosulfate ranges from about 25 mM to about 100 mM, from, about 25 mM to about 75 mM, or from about 25 mM to about 50 mM.

In some embodiments, the method involves (a) isolating the hand, foot, and mouth virus preparation from one or more non-human cells that are used to produce the virus preparation; (b) treating the virus preparation with an effective amount of beta-propiolactone (BPL); and, optionally, (c) treating the virus preparation with an effective amount of formalin concurrently with or after step (b). Alternatively, in some embodiments, the method involves (a) isolating the hand, foot, and mouth virus preparation from one or more non-human cells that are used to produce the virus preparation; (b) treating the virus preparation with an effective amount of beta-propiolactone (BPL) for a first period of time; and (c) treating the virus preparation with an effective amount of BPL for a second period of time to completely inactivate the virus preparation. In some embodiments the first and/or second period of time ranges from about 12 hours to about 36 hours. In certain embodiments the first and/or second period of time is about 24 hours. In certain embodiments, treating with an effective amount of BPL includes, without limitation, treating with BPL in an amount that ranges from about 0.05% v/v to about 3.0% v/v, from 0.1% v/v to about 2% v/v, or about 0.1% v/v to about 1% v/v. In certain embodiments, treating with an effective amount of BPL includes, without limitation, treating with 0.05% v/v, 0.06% v/v, 0.07% v/v, 0.08% v/v, 0.09% v/v, 0.1% v/v, 0.2% v/v, 0.3% v/v, 0.4% v/v, 0.5% v/v, 0.6% v/v, 0.7% v/v, 0.8% v/v, 0.9% v/v, or 1% v/v BPL. In certain embodiments, the isolated and treated virus is selected from one or more of EV71, CA6, and CA16. In certain embodiments of the method, the virus preparation is treated with BEI at a temperature that ranges from about 2° C. to about 8° C. In certain embodiments, the method involves heating the virus preparation at a temperature of 37° C. for a period of time sufficient to hydrolyze the BPL. In certain embodiments, the period of time ranges from about 1 hour to about 6 hours. Alternatively, in some embodiments, the method further involves inactivating (i.e., hydrolyzing) unreacted BPL with an effective amount of sodium thiosulfate. In some embodiments, the effective amount of sodium thiosulfate ranges from about 25 mM to about 100 mM, from, about 25 mM to about 75 mM, or from about 25 mM to about 50 mM.

In some embodiments, the method involves (a) isolating the hand, foot, and mouth virus preparation from one or more non-human cells that are used to produce the virus preparation; (b) treating the virus preparation with an effective amount of formalin; and (c) purifying the virus preparation from the formalin. In certain embodiments, treating with an effective amount of formalin includes, without limitation, treating with formalin in an amount that ranges from about 0.05% v/v to about 3.0% v/v, from 0.1% v/v to about 2% v/v, or about 0.1% v/v to about 1% v/v. In certain embodiments, the isolated and formalin treated virus is selected from one or more of EV71, CA6, and CA16. In certain embodiments, the virus preparation is purified to a high degree from the formalin in an amount that is about 70%, about 75%, about 80%, about 85%, about 90%, about 95%, about 96%, about 97%, about 98%, about 99%, or more.

The vaccines and/or immunogenic compositions of the present disclosure containing one or more antigens from at least one inactivated virus that causes hand, foot and mouth disease, may be useful for treating or preventing hand, foot, and mouth disease in a subject in need thereof and/or inducing an immune response, such as a protective immune response, against hand, foot, and mouth disease in a subject in need thereof.

Formulations of Vaccines and/or Immunogenic Compositions

Further aspects of the present disclosure relate to formulations of vaccines and/or immunogenic compositions of the present disclosure containing one or more antigens from at least one virus that causes hand, foot and mouth disease. Such vaccines and/or immunogenic compositions of the present disclosure containing one or more antigens from at least one virus that causes hand, foot and mouth disease, may be useful for treating or preventing hand, foot, and mouth disease in a subject in need thereof and/or inducing an immune response, such as a protective immune response, against hand, foot, and mouth disease in a subject in need thereof.

Typically, vaccines and/or immunogenic compositions of the present disclosure are prepared as injectables either as liquid solutions or suspensions; solid forms suitable for solution in, or suspension in, liquid prior to injection may also be prepared. Such preparations may also be emulsified or produced as a dry powder. The active immunogenic ingredient is often mixed with excipients which are pharmaceutically acceptable and compatible with the active ingredient. Suitable excipients are, for example, water, saline, dextrose, sucrose, glycerol, ethanol, or the like, and combinations thereof. In addition, if desired, the vaccine or immunogenic composition may contain auxiliary substances such as wetting or emulsifying agents, pH buffering agents, or adjuvants which enhance the effectiveness of the vaccine or immunogenic composition.

Vaccines or immunogenic compositions may be conventionally administered parenterally, by injection, for example, either subcutaneously, transcutaneously, intradermally, subdermally or intramuscularly. Additional formulations which are suitable for other modes of administration include suppositories and, in some cases, oral, peroral, intranasal, buccal, sublingual, intraperitoneal, intravaginal, anal and intracranial formulations. For suppositories, traditional binders and carriers may include, for example, polyalkalene glycols or triglycerides; such suppositories may be formed from mixtures containing the active ingredient in the range of 0.5% to 10%, or even 1-2%. In certain embodiments, a low melting wax, such as a mixture of fatty acid glycerides or cocoa butter is first melted and the hand, foot, and mouth disease vaccine or immunogenic composition antigens described herein are dispersed homogeneously, for example, by stirring. The molten homogeneous mixture is then poured into conveniently sized molds, allowed to cool, and to solidify.

Formulations suitable for intranasal delivery include liquids (e.g., aqueous solution for administration as an aerosol or nasal drops) and dry powders (e.g. for rapid deposition within the nasal passage). Formulations include such normally employed excipients as, for example, pharmaceutical grades of mannitol, lactose, sucrose, trehalose, xylitol, and chitosan. Mucosadhesive agents such as chitosan can be used in either liquid or powder formulations to delay mucociliary clearance of intranasally-administered formulations. Sugars such as mannitol and sucrose can be used as stability agents in liquid formulations and as stability, bulking, or powder flow and size agents in dry powder formulations. In addition, adjuvants such as monophosphoryl lipid A (MLA), or derivatives thereof, or CpG oligonucleotides can be used in both liquid and dry powder formulations as an immunostimulatory adjuvant.

Formulations suitable for oral delivery include liquids, solids, semi-solids, gels, tablets, capsules, lozenges, and the like. Formulations suitable for oral delivery include tablets, lozenges, capsules, gels, liquids, food products, beverages, nutraceuticals, and the like. Formulations include such normally employed excipients as, for example, pharmaceutical grades of mannitol, lactose, starch, magnesium stearate, sodium saccharine, cellulose, magnesium carbonate, and the like. Other hand, foot, and mouth disease vaccine and immunogenic compositions may take the form of solutions, suspensions, pills, sustained release formulations or powders and contain 10-95% of active ingredient, or 25-70%. For oral formulations, cholera toxin is an interesting formulation partner (and also a possible conjugation partner).

The hand, foot, and mouth disease vaccines and/or immunogenic compositions when formulated for vaginal administration may be in the form of pessaries, tampons, creams, gels, pastes, foams or sprays. Any of the foregoing formulations may contain agents in addition to hand, foot, and mouth disease vaccine and immunogenic composition antigens, such as carriers, known in the art to be appropriate.

In some embodiments, the hand, foot, and mouth disease vaccines and/or immunogenic compositions of the present disclosure may be formulated for systemic or localized delivery. Such formulations are well known in the art. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Systemic and localized routes of administration include, e.g., intradermal, topical application, intravenous, intramuscular, etc.

The vaccines and/or immunogenic compositions of the present disclosure may be administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with an exemplary range from about 0.1 μg to 10 μg (even though higher amounts in the 1-10 mg range are contemplated), such as in the range from about 0.1 μg to 5 μg, or even in the range from 0.6 μg to 3 μg or in the range from about 1 μg to 3 μg, or even in the range of 0.1 μg to 1 μg. In certain embodiments, the dosage can be about 0.1 μg, about 0.2 μg, about 0.3 μg, about 0.4 μg, about 0.5 μg, about 0.6 μg, about 0.7 μg, about 0.8 μg, about 0.9 μg, about 1 μg, about 1.1 μg, about 1.2 μg, about 1.3 μg, about 1.4 μg, about 1.5 μg, about 1.6 μg, about 1.7 μg, about 1.8 μg, about 1.9 μg, about 2 μg, about 2.1 μg, about 2.2 μg, about 2.3 μg, about 2.4 μg, about 2.5 μg, about 2.6 μg, about 2.7 μg, about 2.8 μg, about 2.9 μg, or about 3 μg per dose. In certain embodiments, vaccines and/or immunogenic compositions of the present disclosure may be administered in an amount of 1 μg per dose. In vaccines and/or immunogenic compositions of the present disclosure that are multivalent, for example divalent or trivalent vaccines and/or immunogenic compositions comprising antigens from two or more of EV71, CA6, and CA16, the dosage of each component is administered at an equivalent dosage ratio (i.e., 1:1 for divalent and 1:1:1 for trivalent vaccines and/or immunogenic compositions).

Suitable regimens for initial administration and booster shots are also variable but are typified by an initial administration followed by subsequent inoculations or other administrations.

The manner of application may be varied widely. Any of the conventional methods for administration of a vaccine or immunogenic composition are applicable. These include oral application on a solid physiologically acceptable base or in a physiologically acceptable dispersion, parenterally, by injection or the like. The dosage of the vaccine or immunogenic composition will depend on the route of administration and will vary according to the age of the person to be vaccinated and the formulation of the antigen. The vaccine or immunogenic composition can have a unit dosage volume of more than 0.5 mL, of 0.5 mL or of less than 0.5 mL, as described herein. For instance, it can be administered at a volume of 0.25 mL.

Delivery agents that improve mucoadhesion can also be used to improve delivery and immunogenicity especially for intranasal, oral or lung based delivery formulations. One such compound, chitosan, the N-deacetylated form of chitin, is used in many pharmaceutical formulations. It is an attractive mucoadhesive agent for intranasal vaccine delivery due to its ability to delay mucociliary clearance and allow more time for mucosal antigen uptake and processing. In addition, it can transiently open tight junctions which may enhance transepithelial transport of antigen to the NALT. In a recent human trial, a trivalent inactivated influenza vaccine administered intranasally with chitosan but without any additional adjuvant yielded seroconversion and HI titers that were only marginally lower than those obtained following intramuscular inoculation.

Chitosan can also be formulated with adjuvants that function well intranasally such as the genetically detoxified *E. coli* heat-labile enterotoxin mutant LTK63. This adds an immunostimulatory effect on top of the delivery and adhesion benefits imparted by chitosan resulting in enhanced mucosal and systemic responses.

Finally, it should be noted that chitosan formulations can also be prepared in a dry powder format that has been shown to improve vaccine stability and result in a further delay in mucociliary clearance over liquid formulations. This was seen in a recent human clinical trial involving an intranasal dry powder diphtheria toxoid vaccine formulated with chitosan in which the intranasal route was as effective as the traditional intramuscular route with the added benefit of secretory IgA responses. The vaccine was also very well tolerated. Intranasal dry powdered vaccines for anthrax containing chitosan and MLA, or derivatives thereof, induce stronger responses in rabbits than intramuscular inoculation and are also protective against aerosol spore challenge.

Intranasal vaccines represent an exemplary formulation as they can affect the upper and lower respiratory tracts in contrast to parenterally administered vaccines which are better at affecting the lower respiratory tract. This can be beneficial for inducing tolerance to allergen-based vaccines and inducing immunity for pathogen-based vaccines.

In addition to providing protection in both the upper and lower respiratory tracts, intranasal vaccines avoid the complications of needle inoculations and provide a means of inducing both mucosal and systemic humoral and cellular responses via interaction of particulate and/or soluble antigens with nasopharyngeal-associated lymphoid tissues (NALT).

Vaccines and/or immunogenic compositions of the present disclosure are pharmaceutically acceptable. They may include components in addition to the antigen and adjuvant e.g. they will typically include one or more pharmaceutical carrier(s) and/or excipient(s). A thorough discussion of such components is available in Gennaro (2000) Remington: The Science and Practice of Pharmacy. 20th edition, ISBN: 0683306472.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccines and/or immunogenic compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine or immunogenic composition will generally be between 5.0 and 8.1, and more typically between 6.0 and 8.0 e.g. 6.5 and 7.5, or between 7.0 and 7.8. A manufacturing process of the present disclosure may therefore include a step of adjusting the pH of the bulk vaccine prior to packaging.

The vaccine or immunogenic composition is preferably sterile. It is preferably non pyrogenic e.g. containing <1 EU (endotoxin unit, a standard measure) per dose, and preferably <0.1 EU per dose. It is preferably gluten free.

In certain embodiments, the vaccines and/or immunogenic compositions of the present disclosure may include a detergent in an effective concentration. In some embodiments, an effective amount of detergent may include without limitation, about 0.00005% v/v to about 5% v/v or about 0.0001% v/v to about 1% v/v. In certain embodiments, an effective amount of detergent is about 0.001% v/v, about 0.002% v/v, about 0.003% v/v, about 0.004% v/v, about 0.005% v/v, about 0.006% v/v, about 0.007% v/v, about 0.008% v/v, about 0.009% v/v, or about 0.01% v/v. Without wishing to be bound by theory, detergents help maintain the vaccines and/or immunogenic compositions of the present disclosure in solution and helps to prevent the vaccines and/or immunogenic compositions from aggregating.

Suitable detergents include, for example, polyoxyethylene sorbitan ester surfactant (known as 'Tweens'), octoxynol (such as octoxynol-9 (Triton X 100) or t octylphenoxypolyethoxyethanol), cetyl trimethyl ammonium bromide ('CTAB'), and sodium deoxycholate, particularly for a split or surface antigen vaccine. The detergent may be present only at trace amounts. Other residual components in trace amounts could be antibiotics (e.g. neomycin, kanamycin, polymyxin B). In some embodiments, the detergent contains polysorbate. In some embodiments, the effective concentration of detergent includes ranges from about 0.00005% v/v to about 5% v/v.

The vaccines and/or immunogenic compositions are preferably stored at between 2° C. and 8° C. They should not be frozen. They should ideally be kept out of direct light. The antigen and emulsion will typically be in admixture, although they may initially be presented in the form of a kit of separate components for extemporaneous admixing. Vaccines and/or immunogenic compositions will generally be in aqueous form when administered to a subject.

Adjuvants

Other aspects of the present disclosure relate to hand, foot, and mouth vaccines and/or immunogenic compositions containing one or more antigens from at least one virus that causes hand, foot and mouth disease in combination with one or more adjuvants. Such adjuvanted vaccines and/or immunogenic compositions of the present disclosure may be useful for treating or preventing hand, foot, and mouth disease in a subject in need thereof and/or inducing an immune response, such as a protective immune response, against hand, foot, and mouth disease in a subject in need thereof.

Various methods of achieving an adjuvant effect for vaccines are known and may be used in conjunction with the hand, foot, and mouth vaccines and/or immunogenic compositions disclosed herein. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9.

In some embodiments, a hand, foot, and mouth vaccine or immunogenic composition includes the antigens and an adjuvant. Antigens may be in a mixture with at least one adjuvant, at a weight-based ratio of from about 10:1 to about $10^{10}$:1 antigen:adjuvant, e.g., from about 10:1 to about 100:1, from about 100:1 to about $10^3$:1, from about $10^3$:1 to about $10^4$:1, from about $10^4$:1 to about $10^5$:1, from about $10^5$:1 to about $10^6$:1, from about $10^6$:1 to about $10^7$:1, from about $10^7$:1 to about $10^8$:1, from about $10^8$:1 to about $10^9$:1, or from about $10^9$:1 to about $10^{10}$:1 antigen:adjuvant. One of skill in the art can readily determine the appropriate ratio through information regarding the adjuvant and routine experimentation to determine optimal ratios.

Exemplary adjuvants may include, but are not limited to, aluminum salts, toll-like receptor (TLR) agonists, monophosphoryl lipid A (MLA), MLA derivatives, synthetic lipid A, lipid A mimetics or analogs, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA). In some embodiments, the adjuvant is MLA or derivatives thereof.

In some embodiments, the adjuvant is an aluminum salt. In some embodiments, the adjuvant includes at least one of alum, aluminum phosphate, aluminum hydroxide, potassium aluminum sulfate, and Alhydrogel 85. In some embodiments, aluminum salt adjuvants of the present disclosure have been found to increase adsorption of the antigens of the HFMD vaccines and/or immunogenic compositions of the present disclosure. Accordingly, in some embodiments, at least 75%, at least 80%, at least 85%, at least 90%, at least 91%, at least 92%, at least 93%, at least 94%, at least 95%, at least 96%, at least 97%, at least 98%, at least 99%, or 100% of the antigen is adsorbed to the aluminum salt adjuvant.

Certain embodiments of the present disclosure include a method for preparing an adjuvanted hand, foot, and mouth vaccine or immunogenic composition, which involves (a) mixing the vaccine or immunogenic composition with an aluminum salt adjuvant, with the vaccine or immunogenic composition including one or more antigens from at least one virus that causes hand, foot, and mouth disease and (b) incubating the mixture under suitable conditions for a period of time that ranges from about 16 hours to about 24 hours, with at least 75%, at least 80%, at least 85%, at least 90%, at least 91%, at least 92%, at least 93%, at least 94%, at least 95%, at least 96%, at least 97%, at least 98%, at least 99%, or 100% of the antigen adsorbed to the aluminum salt adjuvant. In certain embodiments of the method, the at least one virus that causes hand, foot, and mouth disease is selected from one or more of EV71, CA6, and CA16. In some embodiments of the method, the mixture is incubated at a temperature that ranges from about 2° C. to about 8° C. In some embodiments of the method, the mixture is incubated under constant mixing using any suitable mixer known in the art. In some embodiments of the method, the mixture is incubated at pH that ranges in value from about 6.5 to about 8, from about 6.8 to about 7 8, from about 6.9 to about 7.6, or from about 7 to about 7.5. In certain preferred embodiments, the mixture is incubated at a neutral pH. In some embodiments of the method, the aluminum salt adjuvant is selected from alum, aluminum phosphate, aluminum hydroxide, potassium aluminum sulfate, and Alhydrogel 85.

Monophosphoryl Lipid A (MLA), a non-toxic derivative of lipid A from *Salmonella*, is a potent TLR-4 agonist that has been developed as a vaccine adjuvant (Evans et al. 2003). In pre-clinical murine studies intranasal MLA has been shown to enhance secretory, as well as systemic, humoral responses (Baldridge et al. 2000; Yang et al. 2002). It has also been proven to be safe and effective as a vaccine adjuvant in clinical studies of greater than 120,000 patients (Baldrick et al., 2002; 2004). MLA stimulates the induction of innate immunity through the TLR-4 receptor and is thus capable of eliciting nonspecific immune responses against a wide range of infectious pathogens, including both gram negative and gram positive bacteria, viruses, and parasites (Baldrick et al. 2004; Persing et al. 2002). Inclusion of MLA in intranasal formulations should provide rapid induction of innate responses, eliciting nonspecific immune responses from viral challenge while enhancing the specific responses generated by the antigenic components of the vaccine.

Accordingly, in one embodiment, the present disclosure provides a composition comprising monophosphoryl lipid A (MLA), 3 De-O-acylated monophosphoryl lipid A (3D-MLA), or a derivative thereof as an enhancer of adaptive and innate immunity. Chemically 3D-MLA is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA). In another embodiment, the present disclosure provides a composition comprising synthetic lipid A, lipid A mimetics or analogs, such as BioMira's PET Lipid A, or synthetic derivatives designed to function like TLR-4 agonists.

Additional exemplary adjuvants include, without limitation, polypeptide adjuvants that may be readily added to the antigens described herein by co-expression with the polypeptide components or fusion with the polypeptide components to produce chimeric polypeptides. Bacterial flagellin, the major protein constituent of flagella, is an adjuvant which has received increasing attention as an adjuvant protein because of its recognition by the innate immune system by the toll-like receptor TLR5 (65). Flagellin signaling through TLR5 has effects on both innate and adaptive immune functions by inducing DC maturation and migration as well as activation of macrophages, neutrophils, and intestinal epithelial cells resulting in production of proinflammatory mediators (66-72).

TLR5 recognizes a conserved structure within flagellin monomers that is unique to this protein and is required for flagellar function, precluding its mutation in response to immunological pressure (73). The receptor is sensitive to a 100 fM concentration but does not recognize intact filaments. Flagellar disassembly into monomers is required for binding and stimulation.

As an adjuvant, flagellin has potent activity for induction of protective responses for heterologous antigens administered either parenterally or intranasally and adjuvant effects for DNA vaccines have also been reported. A Th2 bias is observed when flagellin is employed which would be appropriate for a respiratory virus such as influenza but no evidence for IgE induction in mice or monkeys has been observed. In addition, no local or systemic inflammatory responses have been reported following intranasal or systemic administration in monkeys. The Th2 character of responses elicited following use of flagellin is somewhat surprising since flagellin signals through TLR5 in a MyD88-dependent manner and all other MyD88-dependent signals through TLRs have been shown to result in a Th1 bias. Importantly, pre-existing antibodies to flagellin have no appreciable effect on adjuvant efficacy making it attractive as a multi-use adjuvant.

A common theme in many recent intranasal vaccine trials is the use of adjuvants and/or delivery systems to improve vaccine efficacy. In one such study an influenza H3 vaccine containing a genetically detoxified *E. coli* heat-labile enterotoxin adjuvant (LT R192G) resulted in heterosubtypic protection against H5 challenge but only following intranasal delivery. Protection was based on the induction of cross neutralizing antibodies and demonstrated important implications for the intranasal route in development of new vaccines.

Cytokines, colony-stimulating factors (e.g., GM-CSF, CSF, and the like); tumor necrosis factor; interleukin-2, -7, -12, interferons and other like growth factors, may also be used as adjuvants as they may be readily included in the hand, foot, and mouth vaccines or immunogenic compositions by admixing or fusion with the polypeptide component.

In some embodiments, the hand, foot, and mouth vaccine and immunogenic compositions disclosed herein may include other adjuvants that act through a Toll-like receptor such as a nucleic acid TLR9 ligand comprising a 5'-TCG-3' sequence; an imidazoquinoline TLR7 ligand; a substituted guanine TLR7/8 ligand; other TLR7 ligands such as Loxoribine, 7-deazadeoxyguanosine, 7-thia-8-oxodeoxyguanosine, Imiquimod (R-837), and Resiquimod (R-848).

Certain adjuvants facilitate uptake of the vaccine molecules by APCs, such as dendritic cells, and activate these. Non-limiting examples are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminum adjuvants; DNA adjuvants; MLA; and an encapsulating adjuvant.

Additional examples of adjuvants include agents such as aluminum salts such as hydroxide or phosphate (alum), commonly used as 0.05 to 0.1 percent solution in buffered saline (see, e.g., Nicklas (1992) Res. Immunol. 143:489-493), admixture with synthetic polymers of sugars (e.g. Carbopol®) used as 0.25 percent solution, aggregation of the protein in the vaccine by heat treatment with temperatures ranging between 70° to 101° C. for 30 second to 2 minute periods respectively and also aggregation by means of cross-linking agents are possible. Aggregation by reactivation with pepsin treated antibodies (Fab fragments) to albumin, mixture with bacterial cells such as *C. parvum* or endotoxins or lipopolysaccharide components of gram-negative bacteria, emulsion in physiologically acceptable oil vehicles such as mannide monooleate (Aracel A) or emulsion with 20 percent solution of a perfluorocarbon (Fluosol-DA) used as a block substitute may also be employed. Admixture with oils such as squalene and IFA may also be used.

DDA (dimethyldioctadecylammonium bromide) is an interesting candidate for an adjuvant, but also Freund's complete and incomplete adjuvants as well as quillaja saponins such as QuilA and QS21 are interesting. Further possibilities include poly[di(earboxylatophenoxy)phosphazene (PCPP) derivatives of lipopolysaccharides such as monophosphoryl lipid A (MLA), muramyl dipeptide (MDP) and threonyl muramyl dipeptide (tMDP). The lipopolysaccharide based adjuvants may also be used for producing a predominantly Th1-type response including, for example, a combination of monophosphoryl lipid A, such as 3-de-O-acylated monophosphoryl lipid A, together with an aluminum salt.

Liposome formulations are also known to confer adjuvant effects, and therefore liposome adjuvants may be used in conjunction with the hand, foot, and mouth disease vaccines and/or immunogenic compositions.

Immunostimulating complex matrix type (ISCOM® matrix) adjuvants may also be used with the hand, foot, and mouth disease vaccine antigens and immunogenic compositions, especially since it has been shown that this type of adjuvants are capable of up-regulating MHC Class II expression by APCs. An ISCOM matrix consists of (optionally fractionated) saponins (triterpenoids) from Quillaja saponaria, cholesterol, and phospholipid. When admixed with the immunogenic protein such as the hand, foot, and mouth disease vaccine or immunogenic composition antigens, the resulting particulate formulation is what is known as an ISCOM particle where the saponin may constitute 60-70% w/w, the cholesterol and phospholipid 10-15% w/w, and the protein 10-15% w/w. Details relating to composition and use of immunostimulating complexes can for example be found in the above-mentioned text-books dealing with adjuvants, but also Morein B et al., 1995, Clin. Immunother. 3: 461-475 as well as Barr I G and Mitchell G F, 1996, Immunol. and Cell Biol. 74: 8-25 provide useful instructions for the preparation of complete immunostimulating complexes.

The saponins, whether or not in the form of iscoms, that may be used in the adjuvant combinations with the hand, foot, and mouth disease vaccine antigens and immunogenic compositions disclosed herein include those derived from the bark of Quillaja Saponaria Molina, termed Quil A, and fractions thereof, described in U.S. Pat. No. 5,057,540 and "Saponins as vaccine adjuvants", Kensil, C. R., Crit Rev Ther Drug Carrier Syst, 1996, 12 (1-2):1-55; and EP 0 362 279 B1. Exemplary fractions of Quil A are QS21, QS7, and QS17.

β-Escin is another hemolytic saponins for use in the adjuvant compositions of the hand, foot, and mouth disease vaccines and/or immunogenic compositions. Escin is described in the Merck index (12th ed: entry 3737) as a mixture of saponins occurring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August; 44(8):1454-1464)). β-escin is also known as aescin.

Another hemolytic saponin for use in the hand, foot, and mouth disease vaccines and/or immunogenic compositions is Digitonin. Digitonin is described in the Merck index ($12^{th}$ Edition, entry 3204) as a saponin, being derived from the seeds of *Digitalis purpurea* and purified according to the procedure described Gisvold et al., J. Am. Pharm. Assoc., 1934, 23, 664; and Ruhenstroth-Bauer, Physiol. Chem., 1955, 301, 621. Its use is described as being a clinical reagent for cholesterol determination.

Another interesting possibility of achieving adjuvant effect is to employ the technique described in Gosselin et al., 1992. In brief, the presentation of a relevant antigen such as an antigen in a hand, foot, and mouth disease vaccines and/or immunogenic compositions of the present disclosure can be enhanced by conjugating the antigen to antibodies (or antigen binding antibody fragments) against the $F_C$ receptors on monocytes/macrophages. Especially conjugates between antigen and anti-$F_C$RI have been demonstrated to enhance immunogenicity for the purposes of vaccination. The antibody may be conjugated to the hand, foot, and mouth disease vaccine or immunogenic composition antigens after generation or as a part of the generation including by expressing as a fusion to any one of the polypeptide components of the hand, foot, and mouth disease vaccine and immunogenic composition antigens.

Other possibilities involve the use of the targeting and immune modulating substances (i.e. cytokines). In addition, synthetic inducers of cytokines such as poly I:C may also be used.

Suitable mycobacterial derivatives may be selected from the group consisting of muramyl dipeptide, complete Freund's adjuvant, RIBI, (Ribi ImmunoChem Research Inc., Hamilton, Mont.) and a diester of trehalose such as TDM and TDE.

Examples of suitable immune targeting adjuvants include CD40 ligand and CD40 antibodies or specifically binding fragments thereof (cf. the discussion above), mannose, a Fab fragment, and CTLA-4.

Examples of suitable polymer adjuvants include a carbohydrate such as dextran, PEG, starch, mannan, and mannose; a plastic polymer; and latex such as latex beads.

Yet another interesting way of modulating an immune response is to include the immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. 12-15, 1998, Seascape Resort, Aptos, Calif."

Oligonucleotides may be used as adjuvants in conjunction with the hand, foot, and mouth disease vaccine and immunogenic composition antigens and may contain two or more dinucleotide CpG motifs separated by at least three or more or even at least six or more nucleotides. CpG-containing oligonucleotides (in which the CpG dinucleotide is unmethylated) induce a predominantly Th1 response. Such oligonucleotides are well known and are described, for example, in WO 96/02555, WO 99/33488 and U.S. Pat. Nos. 6,008,200 and 5,856,462.

Such oligonucleotide adjuvants may be deoxynucleotides. In certain embodiments, the nucleotide backbone in the oligonucleotide is phosphorodithioate, or a phosphorothioate bond, although phosphodiester and other nucleotide backbones such as PNA including oligonucleotides with mixed backbone linkages may also be used. Methods for producing phosphorothioate oligonucleotides or phosphorodithioate are described in U.S. Pat. Nos. 5,666,153, 5,278,302 and WO95/26204.

Exemplary oligonucleotides have the following sequences. The sequences may contain phosphorothioate modified nucleotide backbones:

```
OLIGO 1:
                                       (SEQ ID NO: 1)
TCC ATG ACG TTC CTG ACG TT (CpG 1826);

OLIGO 2:
                                       (SEQ ID NO: 2)
TCT CCC AGC GTG CGC CAT (CpG 1758);

OLIGO 3:
                                       (SEQ ID NO: 3)
ACC GAT GAC GTC GCC GGT GAC GGC ACC ACG;

OLIGO 4:
                                       (SEQ ID NO: 4)
TCG TCG TTT TGT CGT TTT GTC GTT (CpG 2006);
and OLIGO 5:
                                       (SEQ ID NO: 5)
TCC ATG ACG TTC CTG ATG CT (CpG 1668)
```

Alternative CpG oligonucleotides include the above sequences with inconsequential deletions or additions thereto. The CpG oligonucleotides as adjuvants may be synthesized by any method known in the art (e.g., EP 468520). For example, such oligonucleotides may be synthesized utilizing an automated synthesizer. Such oligonucleotide adjuvants may be between 10-50 bases in length. Another adjuvant system involves the combination of a CpG-containing oligonucleotide and a saponin derivative particularly the combination of CpG and QS21 is disclosed in WO 00/09159.

Many single or multiphase emulsion systems have been described. One of skill in the art may readily adapt such emulsion systems for use with hand, foot, and mouth disease vaccine and immunogenic composition antigens so that the emulsion does not disrupt the antigen's structure. Oil in water emulsion adjuvants per se have been suggested to be useful as adjuvant compositions (EPO 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B).

The oil emulsion adjuvants for use with the hand, foot, and mouth disease vaccines and/or immunogenic compositions described herein may be natural or synthetic, and may be mineral or organic. Examples of mineral and organic oils will be readily apparent to one skilled in the art.

In order for any oil in water composition to be suitable for human administration, the oil phase of the emulsion system may include a metabolizable oil. The meaning of the term metabolizable oil is well known in the art. Metabolizable can be defined as "being capable of being transformed by metabolism" (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils may also be used and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and may be used with the hand, foot, and mouth disease vaccine and immunogenic composition antigens. Squalene is a metabolizable oil virtue of the fact that it is an intermediate in the biosynthesis of cholesterol (Merck index, 10th Edition, entry no. 8619).

Exemplary oil emulsions are oil in water emulsions, and in particular squalene in water emulsions.

In addition, the oil emulsion adjuvants for use with the hand, foot, and mouth disease vaccine and immunogenic composition antigens may include an antioxidant, such as the oil α-tocopherol (vitamin E, EP 0 382 271 B1).

WO 95/17210 and WO 99/11241 disclose emulsion adjuvants based on squalene, α-tocopherol, and TWEEN 80™, optionally formulated with the immunostimulants QS21 and/or 3D-MLA. WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilize the emulsion (WO 98/56414).

The size of the oil droplets found within the stable oil in water emulsion may be less than 1 micron, may be in the range of substantially 30-600 nm, substantially around 30-500 nm in diameter, or substantially 150-500 nm in diameter, and in particular about 150 nm in diameter as measured by photon correlation spectroscopy. In this regard, 80% of the oil droplets by number may be within these ranges, more than 90% or more than 95% of the oil droplets by number are within the defined size ranges. The amounts of the components present in oil emulsions are conventionally in the range of from 2 to 10% oil, such as squalene; and when present, from 2 to 10% alpha tocopherol; and from 0.3 to 3% surfactant, such as polyoxyethylene sorbitan monooleate. The ratio of oil: alpha tocopherol may be equal or less than 1 as this provides a more stable emulsion. SPAN 85™ may also be present at a level of about 1%. In some cases it may be advantageous that the hand, foot, and mouth disease vaccines and/or immunogenic compositions disclosed herein will further contain a stabilizer.

The method of producing oil in water emulsions is well known to one skilled in the art. Commonly, the method includes the step of mixing the oil phase with a surfactant such as a PBS/TWEEN80® solution, followed by homogenization using a homogenizer, it would be clear to one skilled in the art that a method comprising passing the mixture twice through a syringe needle would be suitable for homogenizing small volumes of liquid. Equally, the emulsification process in microfluidizer (M110S microfluidics machine, maximum of 50 passes, for a period of 2 minutes at maximum pressure input of 6 bar (output pressure of about 850 bar)) could be adapted by one skilled in the art to produce smaller or larger volumes of emulsion. This adaptation could be achieved by routine experimentation comprising the measurement of the resultant emulsion until a preparation was achieved with oil droplets of the required diameter.

Alternatively the hand, foot, and mouth disease vaccines and/or immunogenic compositions may be combined with vaccine vehicles composed of chitosan (as described above) or other polycationic polymers, polylactide and polylactide-coglycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM.

Additional illustrative adjuvants for use in the hand, foot, and mouth disease vaccines and/or immunogenic compositions as described herein include SAF (Chiron, Calif., United States), MF-59 (Chiron, see, e.g., Granoff et al. (1997) Infect Immun. 65 (5):1710-1715), the SBAS series of adjuvants (e.g., SB-AS2 (an oil-in-water emulsion containing MLA and QS21); SBAS-4 (adjuvant system containing alum and MLA), available from SmithKline Beecham, Rixensart, Belgium), Detox (Enhanzyn®) (GlaxoSmithKline), RC-512, RC-522, RC-527, RC-529, RC-544, and RC-560 (GlaxoSmithKline) and other aminoalkyl glucosaminide 4-phosphates (AGPs), such as those described in pending U.S. patent application Ser. Nos. 08/853,826 and 09/074,720.

Other examples of adjuvants include, but are not limited to, Hunter's TiterMax® adjuvants (CytRx Corp., Norcross, Ga.); Gerbu adjuvants (Gerbu Biotechnik GmbH, Gaiberg, Germany); nitrocellulose (Nilsson and Larsson (1992) Res. Immunol. 143:553-557); alum (e.g., aluminum hydroxide, aluminum phosphate) emulsion based formulations including mineral oil, non-mineral oil, water-in-oil or oil-in-water emulsions, such as the Seppic ISA series of Montamide adjuvants (e.g., ISA-51, ISA-57, ISA-720, ISA-151, etc.; Seppic, Paris, France); and PROVAX® (IDEC Pharmaceuticals); OM-174 (a glucosamine disaccharide related to lipid A); *Leishmania* elongation factor; non-ionic block copolymers that form micelles such as CRL 1005; and Syntex Adjuvant Formulation. See, e.g., O'Hagan et al. (2001) Biomol Eng. 18(3):69-85; and "Vaccine Adjuvants: Preparation Methods and Research Protocols" D. O'Hagan, ed. (2000) Humana Press.

Other exemplary adjuvants include adjuvant molecules of the general formula:

$$HO(CH_2CH_2O)_n\text{-}A\text{-}R, \qquad (I)$$

where, n is 1-50, A is a bond or —C(O)—, R is $C_{1\text{-}50}$ alkyl or Phenyl $C_{1\text{-}50}$ alkyl.

One embodiment consists of a vaccine formulation comprising a polyoxyethylene ether of general formula (I), where n is between 1 and 50, 4-24, or 9; the R component is $C_{1\text{-}50}$, $C_4$-$C_{20}$ alkyl, or $C_{12}$ alkyl, and A is a bond. The concentration of the polyoxyethylene ethers should be in the range 0.1-20%, from 0.1-10%, or in the range 0.1-1%. Exemplary polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, an adjuvant combination may include the CpG as described above.

Further examples of suitable pharmaceutically acceptable excipients for use with the hand, foot, and mouth disease vaccines and/or immunogenic compositions disclosed herein include water, phosphate buffered saline, isotonic buffer solutions.

Methods of the Present Disclosure

Further aspects of the present disclosure relate to methods for using vaccines and/or or immunogenic compositions of the present disclosure containing one or more antigens from at least one virus that causes hand, foot and mouth disease to treat or prevent hand, foot, and mouth disease in a subject in need thereof and/or to induce an immune response to hand, foot, and mouth disease in a subject in need thereof. In some embodiments, the present disclosure relates to methods for treating or preventing hand, foot, and mouth disease in a subject in need thereof by administering to the subject a therapeutically effective amount of a vaccine and/or or immunogenic composition of the present disclosure containing one or more antigens from at least one virus that causes hand, foot and mouth disease. In some embodiments, the present disclosure relates to methods for inducing an immune response to hand, foot, and mouth disease in a subject in need thereof by administering to the subject a therapeutically effective amount of a vaccine and/or or immunogenic composition of the present disclosure containing one or more antigens from at least one virus that causes hand, foot and mouth disease.

In some embodiments, the protective immune response includes an immune response against one or more of EV71, CA6, and CA16. In some embodiments, the protective immune response includes an immune response against one or more EV71 viral genotypes such as B4, C2, C4, and C5.

The hand, foot, and mouth disease vaccines and/or immunogenic compositions disclosed herein may be used to protect or treat a mammal or bird susceptible to, or suffering from a viral infection, by means of administering the vaccine by intranasal, peroral, oral, buccal, sublingual, intramuscular, intraperitoneal, intradermal, transdermal, subdermal, intravaginal, anal, intracranial, intravenous, transcutaneous, or subcutaneous administration. Methods of systemic administration of the vaccines and/or immunogenic compositions of the present disclosure may include conventional syringes and needles, or devices designed for ballistic delivery of solid vaccines (WO 99/27961), or needleless pressure liquid jet device (U.S. Pat. Nos. 4,596,556; 5,993,412), or transdermal patches (WO 97/48440; WO 98/28037). The hand, foot, and mouth disease vaccines and/or immunogenic compositions of the present disclosure may also be applied to the skin (transdermal or transcutaneous delivery WO 98/20734; WO 98/28037). The hand, foot, and mouth disease vaccines and/or immunogenic compositions of the present disclosure therefore may include a delivery device for systemic administration, pre-filled with the hand, foot, and mouth disease vaccine or immunogenic compositions. Accordingly there is provided methods for treating or preventing hand, foot, and mouth disease and for inducing an immune response in a subject such as a mammal or bird, including the step of administering a vaccine or immunogenic composition of the present disclosure and optionally including an adjuvant and/or a carrier, to the subject, where the vaccine or immunogenic composition is administered via the parenteral or systemic route.

The vaccines and/or immunogenic compositions of the present disclosure may be used to protect or treat a mammal or bird susceptible to, or suffering from a viral infection, by means of administering the vaccine or immunogenic composition via a mucosal route, such as the oral/alimentary or nasal route. Alternative mucosal routes are intravaginal and intra-rectal. The mucosal route of administration may be via the nasal route, termed intranasal vaccination. Methods of intranasal vaccination are well known in the art, including the administration of a droplet, spray, or dry powdered form of the vaccine into the nasopharynx of the individual to be immunized. Nebulized or aerosolized vaccine formulations are potential forms of the hand, foot, and mouth disease vaccines and/or immunogenic compositions disclosed herein. Enteric formulations such as gastro resistant capsules and granules for oral administration, suppositories for rectal or vaginal administration are also formulations of the vaccines and/or immunogenic compositions of the present disclosure.

The hand, foot, and mouth disease vaccines and/or immunogenic compositions of the present disclosure may also be administered via the oral route. In such cases the pharmaceutically acceptable excipient may also include alkaline buffers, or enteric capsules or microgranules. The hand, foot, and mouth disease vaccines and/or immunogenic compositions of the present disclosure may also be administered by the vaginal route. In such cases, the pharmaceutically acceptable excipients may also include emulsifiers, polymers such as CARBOPOL®, and other known stabilizers of vaginal creams and suppositories. The hand, foot, and mouth disease vaccines and/or immunogenic compositions may also be administered by the rectal route. In such cases the excipients may also include waxes and polymers known in the art for forming rectal suppositories.

In some embodiments, the administering step includes one or more administrations. Administration can be by a single dose schedule or a multiple dose (prime-boost) schedule. In a multiple dose schedule the various doses may be given by the same or different routes e.g. a parenteral prime and mucosal boost, a mucosal prime and parenteral boost, etc. Typically they will be given by the same route. Multiple doses will typically be administered at least 1 week apart (e.g. about 2 weeks, about 3 weeks, about 4 weeks, about 6 weeks, about 8 weeks, about 12 weeks, about 16 weeks, etc.). Giving two doses separated by from 25-30 days (e.g. 28 days) is particularly useful.

The methods of the present disclosure include administration of a therapeutically effective amount or an immunogenic amount of the vaccines and/or immunogenic compositions of the present disclosure. A therapeutically effective amount or an immunogenic amount may be an amount of the vaccines and/or immunogenic compositions of the present disclosure that will induce a protective immunological response in the uninfected, infected or unexposed subject to which it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the therapeutically effective amount or immunogenic amount is sufficient to bring about treatment or prevention of disease symptoms. The exact amount necessary will vary depending on the subject being treated; the age and general condition of the subject to be treated; the capacity of the subject's immune system to synthesize antibodies; the degree of protection desired; the severity of the condition being treated; the particular hand, foot, and mouth disease antigen polypeptide selected and its mode of administration, among other factors. An appropriate therapeutically effective amount or immunogenic amount can be readily determined by one of skill in the art. A therapeutically effective amount or immunogenic amount will fall in a relatively broad range that can be determined through routine trials.

ENUMERATED EMBODIMENTS

The following enumerated embodiments are representative of some aspects of the invention.

1. A hand, foot, and mouth vaccine comprising one or more antigens from at least one inactivated virus that causes hand, foot and mouth disease in humans, wherein the at least one virus was inactivated with BEI.
2. A hand, foot, and mouth immunogenic composition comprising one or more antigens from at least one inactivated virus that causes hand, foot and mouth disease in humans, wherein the at least one virus was inactivated with BEI.
3. The vaccine or immunogenic composition of embodiment 1 or embodiment 2, wherein the at least one virus inactivated by BEI comprises one or more modifications.
4. The vaccine or immunogenic composition of embodiment 3, wherein the one or more modifications comprise a modified nucleic acid.
5. The vaccine or immunogenic composition of embodiment 4, wherein the modified nucleic acid is an alkylated nucleic acid.
6. The vaccine or immunogenic composition of any one of embodiments 1-5, wherein unreacted BEI was hydrolyzed with sodium thiosulfate.
7. The vaccine or immunogenic composition of any one of embodiments 1-6, wherein the at least one virus is selected from one or more of EV71, CA6, and CA16.
8. The vaccine or immunogenic composition of any one of embodiments 1-6, wherein the at least one virus comprises EV71, CA6, and CA16.

9. The vaccine or immunogenic composition of any one of embodiments 1-6, wherein the at least one virus comprises EV71 and CA6.

10. The vaccine or immunogenic composition of any one of embodiments 1-6, wherein the at least one virus comprises EV71 and CA16.

11. The vaccine or immunogenic composition of any one of embodiments 1-6, wherein the at least one virus comprises CA6 and CA16.

12. The vaccine or immunogenic composition of any one of embodiments 1-6, wherein the at least one virus is EV71.

13. The vaccine or immunogenic composition of any one of embodiments 1-6, wherein the one or more antigens are selected from EV71, CA6, CA16, and any combination thereof.

14. The vaccine or immunogenic composition of embodiment 13, wherein the one or more antigens are from EV71.

15. The vaccine or immunogenic composition of any one of embodiments 1-14, wherein the one or more antigens comprise at least one non-human cell adaptation mutation.

16. The vaccine or immunogenic composition of embodiment 15, wherein the one or more antigens comprise the VP1 polypeptide of EV71, and wherein the VP1 polypeptide comprises the at least one non-human cell adaptation mutation.

17. The vaccine or immunogenic composition of any one of embodiments 1-16, wherein the one or more antigens comprise the VP1 polypeptide of CA6 and wherein the VP1 polypeptide comprises the at least one non-human cell adaptation mutation.

18. The vaccine or immunogenic composition of any one of embodiments 1-17, wherein the one or more antigens comprise the VP2 polypeptide of CA6, and where in the VP2 polypeptide comprises the at least one non-human cell adaptation mutation.

19. The vaccine or immunogenic composition of any one of embodiments 1-18, wherein the one or more antigens comprise the VP3 polypeptide of CA6, and wherein the VP3 polypeptide comprises the at least one non-human cell adaptation mutation.

20. The vaccine or immunogenic composition of any one of embodiments 1-19, wherein the one or more antigens comprise the 5' untranslated region (UTR) of CA6, and wherein the 5' UTR of CA6 comprises the at least one non-human cell adaptation mutation.
21. The vaccine or immunogenic composition of any one of embodiments 1-20, wherein the one or more antigens comprise the 2A polypeptide of CA16, and wherein the 2A polypeptide comprises the at least one non-human cell adaptation mutation.
22. The vaccine or immunogenic composition of any one of embodiments 1-21, wherein the one or more antigens comprise the VP2 polypeptide of CA16, and wherein the VP2 polypeptide comprises the at least one non-human cell adaptation mutation.
23. The vaccine or immunogenic composition of any one of embodiments 1-22, wherein the one or more antigens comprise the VP1 polypeptide of CA16, and wherein the VP1 polypeptide comprises the at least one non-human cell adaptation mutation.
24. The vaccine or immunogenic composition of any one of embodiments 1-23, wherein the one or more antigens comprise the 5' untranslated region (UTR) of CA16 and wherein the 5' UTR of CA16 comprises the at least one non-human cell adaptation mutation.
25. The vaccine or immunogenic composition of any one of embodiments 1-24, wherein the non-human cell is a mammalian cell.
26. The vaccine or immunogenic composition of any one of embodiments 1-24, wherein the non-human cell is a monkey cell.
27. The vaccine or immunogenic composition of embodiment 26, wherein the monkey cell is a from a Vero cell line.
28. The vaccine or immunogenic composition of embodiment 27, wherein the Vero cell line is selected from WHO Vero 10-87, ATCC CCL-81, Vero 76 (ATCC Accession No. CRL-1587), and Vero C1008 (ATCC Accession No. CRL-1586).
29. The vaccine or immunogenic composition of any one of embodiments 1-28, wherein the one or more antigens were produced by culturing the non-human cell.
30. The vaccine or immunogenic composition of embodiment 29, wherein the cell was cultured in serum-free media.
31. The vaccine or immunogenic composition of any one of embodiments 1-30, wherein the vaccine or immunogenic composition is a purified antigen vaccine or immunogenic composition, a subunit vaccine or immunogenic composition, or an attenuated virus vaccine or immunogenic composition.
32. The vaccine or immunogenic composition of any one of embodiments 1-31, further comprising a detergent in an effective concentration.
33. The vaccine or immunogenic composition of embodiment 32, wherein the detergent comprises polysorbate [80].
34. The vaccine or immunogenic composition of embodiment 33, wherein the effective concentration is about from about 0.001% to about 0.01%.
35. The vaccine or immunogenic composition of any one of embodiments 1-34, further comprising an adjuvant.
36. The vaccine or immunogenic composition of embodiment 35, wherein the adjuvant is selected from the group consisting of aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA).
37. The vaccine or immunogenic composition of embodiment 36, wherein the adjuvant is an aluminum salt.
38. The vaccine or immunogenic composition of embodiment 36, wherein the adjuvant is selected from alum, aluminum phosphate, aluminum hydroxide, potassium aluminum sulfate, and Alhydrogel 85.
39. The vaccine or immunogenic composition of embodiment 37 or embodiment 38, wherein at least 75%, at least 80%, at least 85%, at least 90%, at 95%, at least 97%, at least 99%, or 100% of the antigen is adsorbed to the adjuvant.
40. A method for treating or preventing hand, foot, and mouth disease in a subject in need thereof, comprising administering to the subject a therapeutically effective amount of the vaccine or immunogenic composition of any one of embodiments 1-39.
41. A method for inducing an immune response in a subject in need thereof, comprising administering to the subject an immunogenic amount of the vaccine or immunogenic composition of any one of embodiments 1-39.
42. The method of embodiment 40 or embodiment 41, wherein the administering induces a protective immune response in the subject.
43. The method of embodiment 42, wherein the immune response comprises an immune response against one or more of EV71, CA6, and CA16.
44. The method of embodiment 42, wherein the immune response comprises an immune response against one or more EV71 viral genotypes selected from B4, C2, C4, and C5.
45. The method of any one of embodiments 40-44, wherein the administering is selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.
46. The method of any one of embodiments 40-45, wherein the administering comprises one or more administrations.
47. A method for inactivating a hand, foot, and mouth virus preparation, comprising:
  (a) isolating the hand, foot, and mouth virus preparation from one or more non-human cells, wherein the cells are used to produce the virus preparation; and
  (b) treating the virus preparation with an effective amount of BEI; and
  wherein the virus is selected from one or more of EV71, CA6, and CA16.
48. The method of embodiment 47, wherein the virus preparation is treated with BEI in an amount that ranges from about 0.25% v/v to about 3.0% v/v.
49. The method of embodiment 47 or embodiment 48, wherein the virus preparation is treated with BEI at a temperature that ranges from about 25° C. to about 42° C.
50. The method of any one of embodiments 47-48, wherein the virus preparation is treated with BEI for a period of time that ranges from about 1 hour to about 10 hours.
51. The method of any one of embodiments 47-50, wherein the method further comprises hydrolyzing unreacted BEI with an effective amount of sodium thiosulfate.
52. The method of embodiment 51, wherein the effective amount of sodium thiosulfate ranges from about 25 mM to about 100 mM.
53. The method of any one of embodiments 47-52, wherein the inactivated virus preparation comprises one or more modifications.
54. The method of embodiment 53, wherein the one or more modifications comprise a modified nucleic acid.
55. The method of embodiment 54, wherein the modified nucleic acid is an alkylated nucleic acid.
56. A hand, foot, and mouth vaccine comprising one or more antigens from at least one virus that causes hand, foot and mouth disease in humans and a detergent in an effective concentration.
57. A hand, foot, and mouth immunogenic composition comprising one or more antigens from at least one virus that causes hand, foot and mouth disease in humans and a detergent in an effective concentration.
58. The vaccine or immunogenic composition of embodiment 56 or embodiment 57, wherein the detergent comprises polysorbate [80].
59. The vaccine or immunogenic composition of any one of embodiments 56-58, wherein the effective concentration ranges from about 0.001% to about 0.01%.
60. The vaccine or immunogenic composition of any one of embodiments 56-59, wherein the at least one virus is selected from one or more of EV71, CA6, and CA16.
61. The vaccine or immunogenic composition of any one of embodiments 56-59, wherein the at least one virus comprises EV71, CA6, and CA16.
62. The vaccine or immunogenic composition of any one of embodiments 56-59, wherein the at least one virus comprises EV71 and CA6.
63. The vaccine or immunogenic composition of any one of embodiments 56-59, wherein the at least one virus comprises EV71 and CA16.
64. The vaccine or immunogenic composition of any one of embodiments 56-59, wherein the at least one virus comprises CA6 and CA16.
65. The vaccine or immunogenic composition of any one of embodiments 56-59, wherein the at least one virus is EV71.
66. The vaccine or immunogenic composition of any one of embodiments 56-59, wherein the one or more antigens are selected from EV71, CA6, CA16, and any combination thereof.
67. The vaccine or immunogenic composition of embodiment 66, wherein the one or more antigens are from EV71.
68. The vaccine or immunogenic composition of any one of embodiments 56-67, wherein the one or more antigens comprise at least one non-human cell adaptation mutation.
69. The vaccine or immunogenic composition of embodiment 68, wherein the one or more antigens comprise the VP1 polypeptide of EV71, and wherein the VP1 polypeptide comprises the at least one non-human cell adaptation mutation.
70. The vaccine or immunogenic composition of embodiment 68, wherein the one or more antigens comprise the 5' untranslated region (UTR) of EV71, and wherein the 5' UTR of EV71 comprises the at least one non-human cell adaptation mutation.
71. The vaccine or immunogenic composition of embodiment 68, wherein the one or more antigens comprise the VP1 polypeptide of CA6 and wherein the VP1 polypeptide comprises the at least one non-human cell adaptation mutation.
72. The vaccine or immunogenic composition of embodiment 68, wherein the one or more antigens comprise the VP2 polypeptide of CA6, and where in the VP2 polypeptide comprises the at least one non-human cell adaptation mutation.
73. The vaccine or immunogenic composition of embodiment 68, wherein the one or more antigens comprise the VP3 polypeptide of CA6, and wherein the VP3 polypeptide comprises the at least one non-human cell adaptation mutation.
74. The vaccine or immunogenic composition of embodiment 68, wherein the one or more antigens comprise the 5' untranslated region (UTR) of CA6, and wherein the 5' UTR of CA6 comprises the at least one non-human cell adaptation mutation.
75. The vaccine or immunogenic composition of embodiment 68, wherein the one or more antigens comprise the 2A polypeptide of CA16, and wherein the 2A polypeptide comprises the at least one non-human cell adaptation mutation.
76. The vaccine or immunogenic composition of embodiment 68, wherein the one or more antigens comprise the VP2 polypeptide of CA16, and wherein the VP2 polypeptide comprises the at least one non-human cell adaptation mutation.

77. The vaccine or immunogenic composition of embodiment 68, wherein the one or more antigens comprise the VP1 polypeptide of CA16, and wherein the VP1 polypeptide comprises the at least one non-human cell adaptation mutation.

78. The vaccine or immunogenic composition of embodiment 68, wherein the one or more antigens comprise the 5' untranslated region (UTR) of CA16, and wherein the 5' UTR of CA16 comprises the at least one non-human cell adaptation mutation.

79. The vaccine or immunogenic composition of any one of embodiments 56-78, wherein the non-human cell is a mammalian cell.

80. The vaccine or immunogenic composition of any one of embodiments 56-78, wherein the non-human cell is a monkey cell.

81. The vaccine or immunogenic composition of embodiment 80, wherein the monkey cell is a from a Vero cell line.

82. The vaccine or immunogenic composition of embodiment 81, wherein the Vero cell line is selected from WHO Vero 10-87, ATCC CCL-81, Vero 76 (ATCC Accession No. CRL-1587), and Vero C1008 (ATCC Accession No. CRL-1586).

83. The vaccine or immunogenic composition of any one of embodiments 56-82, wherein the one or more antigens were produced by culturing the non-human cell.

84. The vaccine or immunogenic composition of embodiment 83, wherein the cell was cultured in serum-free media.

85. The vaccine or immunogenic composition of any one of embodiments 56-84, wherein the vaccine or immunogenic composition is a purified antigen vaccine or immunogenic composition, a subunit vaccine or immunogenic composition, or an attenuated virus vaccine or immunogenic composition.

86. The vaccine or immunogenic composition of any one of embodiments 56-85, wherein the at least one virus was chemically inactivated.

87. The vaccine or immunogenic composition of embodiment 86, wherein the at least one virus was chemically inactivated with one or more of beta-propiolactone (BPL), formalin, or binary ethylenimine (BEI).

88. The vaccine or immunogenic composition of embodiment 86, wherein the at least one virus was chemically inactivated with BEI.

89. The vaccine or immunogenic composition of 88, wherein the at least one virus inactivated by BEI comprises one or more modifications.

90. The vaccine or immunogenic composition of embodiment 89, wherein the one or more modifications comprise a modified nucleic acid.

91. The vaccine or immunogenic composition of embodiment 90, wherein the modified nucleic acid is an alkylated nucleic acid.

92. The vaccine or immunogenic composition of any one embodiments 88-91, wherein unreacted BEI was hydrolyzed with sodium thiosulfate.

93. The vaccine or immunogenic composition of any one of embodiments 56-92, further comprising an adjuvant.

94. The vaccine or immunogenic composition of embodiment 93, wherein the adjuvant is selected from the group consisting of aluminum salts, toll-like receptor (TLR) agonists, monophosphoryl lipid A (MLA), synthetic lipid A, lipid A mimetics or analogs, MLA derivatives, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, Complete Freund's Adjuvant (CFA), and Incomplete Freund's Adjuvant (IFA).

95. The vaccine or immunogenic composition of embodiment 94, wherein the adjuvant is an aluminum salt.

96. The vaccine or immunogenic composition of embodiment 94, wherein the adjuvant is selected from alum, aluminum phosphate, aluminum hydroxide, potassium aluminum sulfate, and Alhydrogel 85.

97. The vaccine or immunogenic composition of embodiment 95 or embodiment 96, wherein at least 75%, at least 80%, at least 85%, at least 90%, at 95%, at least 97%, at least 99%, or 100% of the antigen is adsorbed to the adjuvant.

98. A method for treating or preventing hand, foot, and mouth disease in a subject in need thereof, comprising administering to the subject a therapeutically effective amount of the vaccine or immunogenic composition of any one of embodiments 56-97.

99. A method for inducing an immune response in a subject in need thereof, comprising administering to the subject an immunogenic amount of the vaccine or immunogenic composition of any one of embodiments 56-97.

100. The method of embodiment 98 or embodiment 99, wherein the administering induces a protective immune response in the subject.

101. The method of embodiment 100, wherein the immune response comprises an immune response against one or more of EV71, CA6, and CA16.

102. The method of embodiment 100, wherein the immune response comprises an immune response against one or more EV71 viral genotypes selected from B4, C2, C4, and C5.

103. The method of any one of embodiments 98-102, wherein the administering is selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.

104. The method of any one of embodiments 98-103, wherein the administering comprises one or more administrations.

The present disclosure will be more fully understood by reference to the following Examples. They should not, however, be construed as limiting any aspect or scope of the present disclosure in any way.

EXAMPLES

Example 1

Evaluation of the Immunogenicity and Safety of Inactivated Enterovirus 71

Introduction

Hand, foot, and mouth disease (HFMD) is caused by several members of the human enterovirus A (HEV-A) group. It is generally a self-limiting infection affecting mostly children and is characterized by ulcers and vesicles on the hands, feet and oral cavity. However, a more severe form of disease may occur with neurological symptoms such as meningitis, encephalitis, polio-like paralysis, and brain stem encephalitis leading to pulmonary edema and death [1]-[3]. Since the mid-1990s, HFMD infections caused by human enterovirus 71 (EV71) have resulted in significant morbidity and mortality, particularly in the Asia-Pacific region [4], [5]. China, Viet Nam, and Singapore reported increased activity in January-May 2012 compared to the same period in 2011 [6]. In addition, HFMD outbreaks disrupt education and economic activities due to school and childcare center closures in efforts to control disease transmission [7].

Human enterovirus A belongs to the Picornaviridae family of non-enveloped, positive-sense RNA viruses, which also includes polioviruses and rhinoviruses. Members of the HEV-A group which cause HFMD include EV71 and Coxsackievirus A16 (CAV16) [8]. HFMD outbreaks due to EV71 infection have the greatest propensity to cause severe neurological disease. Experimental infection of cynomolgus macaques showed that strains isolated across several decades were all neurotropic, as well as showing a broader tissue tropism than polioviruses [9].

Enterovirus 71 has four capsid proteins (VP1-VP4) and seven nonstructural proteins. In addition to protecting the viral RNA, the capsid proteins recognize receptors on the surface of host cells and contribute to the antigenic profile of the virus [8]. Known human cell surface receptors for EV71 are the scavenger receptor B2 (SCARB2), and the P-selectin glycoprotein ligand 1 (PSGL-1) [10], [11].

Although the classical method of typing enteroviruses by serum neutralization defines EV71 as a single serotype [12], current molecular typing methods indicate that several genogroups have been circulating in the Asia-Pacific region at least since the 1990s [13]. EV71 isolates were previously classified into genogroups A, B, and C and sub-genogroups based on VP1 nucleotide sequences alone [14]; nucleotide sequence identity of the VP1 gene is >92% within genogroups, whereas nucleotide sequence identity between the genogroups is 78-83% [4]. However, whole-genome sequencing resulted in the reclassification of subgenogroup B5 under B4 and addition of genogroup D; the authors suggested that the 3D polymerase sequence together with VP1 better represented whole genomes [15]. Recombination between genogroups and with other Human enterovirus A serotypes also occurs [16].

At present there is no specific antiviral therapy or vaccine available against EV71. Intravenous immunoglobulin has been used in severe HFMD cases, with some therapeutic benefit suggested by the outcomes but as yet unproven by clinical trials [3], [17]. Preventive and control measures during EV71 outbreaks are limited to surveillance, closure of educational and childcare facilities, and isolation of patients. Candidate vaccines under development include formaldehyde-inactivated whole-virus vaccine [18], [19], VP1 subunit vaccines [20], [21], a peptide-based synthetic vaccine [22], a recombinant bacterial-vectored VP1-based vaccine [23], a plasmid DNA vaccine expressing VP1 [24], virus-like particles of EV71 [25], and a live—attenuated vaccine [26]. Common findings include the necessity for an adjuvant [27], and the use of whole virus particles as opposed to recombinant proteins or short peptides alone [28]. Human clinical trials of inactivated virus vaccines producing high neutralizing antibody titers have been conducted in China [29], [30], Taiwan [31], and Singapore.

The following Example demonstrates the development of an inactivated EV71 vaccine in animal models and an evaluation of its immunogenicity and safety are described.

Materials and Methods
Viruses and Cell Culture

The genogroup B EV71 strain, MS/7423/87 (GenBank accession number U22522.1) was selected to prepare the vaccine on the basis of amino acid sequence similarity to highly immunogenic strains as well as high yield in Vero cell culture.

The vaccine strain was grown in Vero cells (WHO Reference Cell Bank 10-87) in 10-tier cell factories as described below, using Dulbecco's Modified Eagle's Medium (DMEM; Sigma-Aldrich, United States) without serum. Small scale preparations for neutralization assays were grown in Vero clone E6 cells (ATCC CRL-1586) in tissue culture flasks (BD Biosciences, United States) using Minimum Essential Medium (MEM; Sigma-Aldrich, United States) with 2% fetal bovine serum (FBS; Biological Industries, Israel).

Inactivated EV71 Virus

Confluent monolayers of Vero cells in 10-tier cell factories (Nalge Nunc International, United States) were infected with the EV71 vaccine strain at a multiplicity of infection (MOI) of 0.1 to 0.01. When cytopathic effect (CPE) was complete, the medium was harvested, clarified by filtration, followed by treatment with benzonase (Merck Chemicals, Germany) to remove host cell nucleic acid at 20 U/mL, 37° C. for 24 hours. The clarified harvest was treated with freshly prepared "binary" ethyleneimine (BEI) at 1.5% v/v, 37° C. for 6 hours to inactivate EV71 infectivity [32], followed by the addition of 150 mM sodium thiosulfate to hydrolyze unreacted ethylenimine. Inactivation of viral infectivity was confirmed at this stage by blind-passaging the material twice on Vero cells. Tissue culture medium components and low molecular weight proteins were partially removed by concentration and diafiltration against phosphate-buffered saline containing 0.002% Tween® 80 (PBST). The inactivated virus preparation was further purified by chromatography using ion-exchange and size-exclusion columns, concentrated using a 30 kDa molecular weight cut-off membrane, and finally sterilized by filtration through a 0.2 µm membrane. Purified inactivated EV71 antigen was stored at −80° C. in suspension in PBST.

Characterization of Purified Inactivated EV71 Antigen

The presence and estimated purity of EV71 antigen in samples were evaluated by SDS-PAGE and Western blotting. Briefly, samples were heated to 95° C. in lithium dodecyl sulfate buffer (Invitrogen) with beta-mercaptoethanol (Sigma-Aldrich) and fractionated on duplicate 4-12% PAGE gels (Invitrogen) in MES-SDS buffer. For purity estimation, one gel was stained with colloidal blue (Invitrogen) followed by image intensity calculations using Quantity One software (Bio-Rad). For detection of EV71 antigens, proteins were transferred to a PVDF membrane using the iBlot semi-dry blotting system (Invitrogen) and stained for the presence of VP2 and VP0 using the monoclonal antibody 422-8D-4C-4D (Merck Millipore, catalogue number MAB979), followed by an HRP-conjugated anti-mouse IgG secondary antibody (DAKO) and DAB substrate (Sigma-Aldrich) to visualize bands.

The physical form of the EV71 antigen present was examined by transmission electron microscopy using a phosphotungstic acid negative stain on carbon formvar grids (Electron Microscopy Services).

Immunization Procedures

In the two following mouse studies, male BALB/c mice between 4-6 weeks old were used. Volumes of 100 µL per dose were administered by intramuscular (IM) injection in the hind leg as two injections of 50 μL in the same leg, due the limitations on the volume of a single injection in mice.

Immunogenicity of EV71 antigen formulated with or without aluminum hydroxide: Groups of mice (n=8) were injected on Days 0 and 28 with the following doses of purified inactivated EV71 antigen (0.12 μg, 0.6 μg, or 3.0 μg) in PBST only or with aluminum hydroxide (Alhydrogel "85", Brenntag Biosector, Denmark) at 0.5 mg (aluminum content) per dose. Two groups of control animals (n=8) were injected with PBST or Alhydrogel (0.5 mg per dose) using the same immunization protocol as above. Blood samples were collected on day 0, 28, 42, 56, 91, and 120; sera were stored at −20° C. until testing for neutralizing activity.

Determination of the optimum immunogenic dose: Groups of mice (n=10) were immunized on days 0 and 28 with the following doses of purified inactivated EV71: 0.12 μg, 0.6 μg, 3 μg, 9 μg, and 15 μg, formulated with Alhydrogel (0.5 mg in a volume of 100 μL per dose). A control group received Alhydrogel alone (0.5 mg per dose in a volume of 100 μL per dose). Blood samples were collected on day 0, 28, and 56; sera were stored at −20° C. until testing for neutralizing activity.

Figure 5:
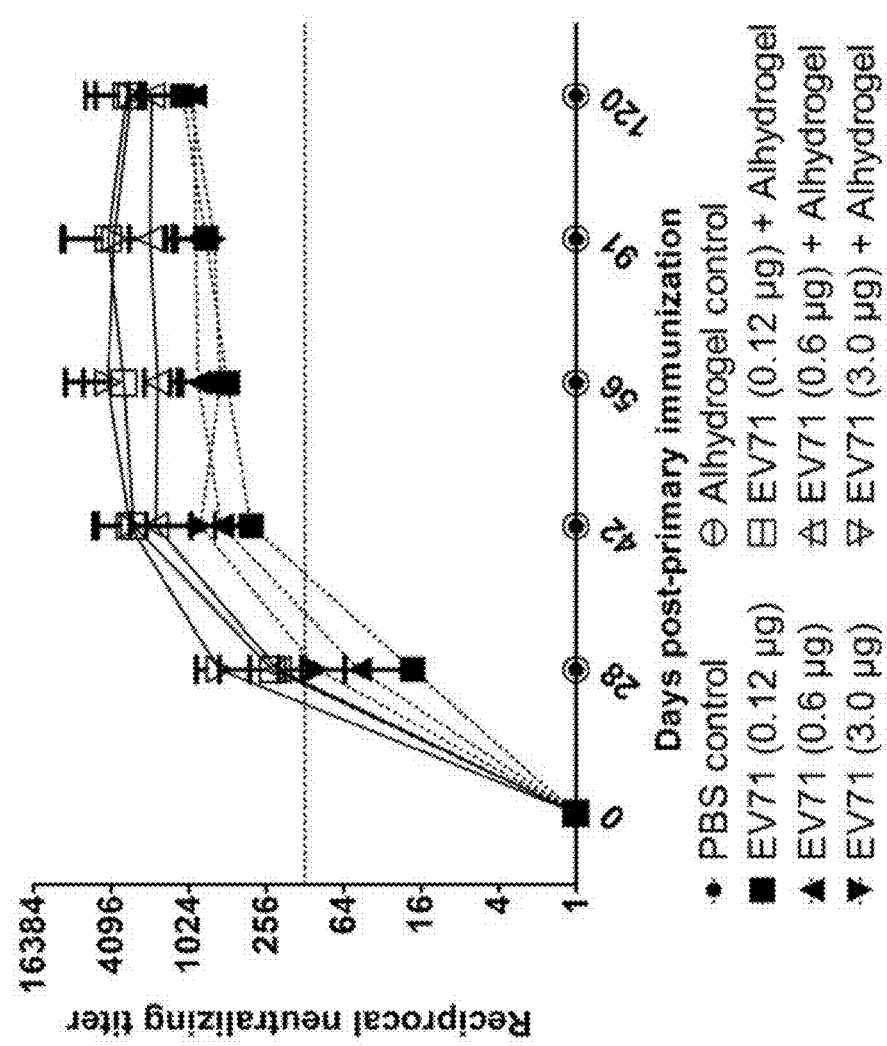

New Zealand White rabbits were used as the test species with females to males at a 1 1 ratio in each group. Low and high dose vaccines were formulated, containing 0.6 μg and 3.0 μg EV71 antigen respectively, with 0.5 mg Alhydrogel in a 0.5 mL volume. Twenty rabbits received each vaccine formulation. Control groups received normal saline (PBS, n=12) or 0.5 mg Alhydrogel alone (vaccine placebo, n=16). Test articles were administered by IM injection in the left thigh. All animals received a booster injection of the same dose and route on day 28; the animals in the high dose group received a second booster on day 42.

Animals were observed for morbidity and mortality at least twice daily during the treatment and observation periods, in addition to weekly clinical examinations. Parameters monitored were: injection site reactogenicity (Draize numerical scoring system), rectal temperature, body mass, food consumption (grams/rabbit/week), ophthalmological examination, and respiratory rate. Half the animals of each sex in each group were sacrificed 2 days after the last immunization, either on Day 30 (low dose, saline placebo, and Alhydrogel placebo groups) or Day 44 (high dose group); the remaining animals were sacrificed on Day 56. Blood samples were collected on Days 0, 3, 28, 42 (high dose group only), and 56 and used for clinical chemistry, hematology, and EV71 neutralizing antibody assays. Gross pathology examinations were performed on all sacrificed animals. A complete necropsy and histopathology examinations were performed on organs from the animals sacrificed on Day 30 (saline placebo, Alhydrogel placebo, and vaccine low dose groups) or Day 44 (high dose group).

Determination of Neutralizing Antibody Responses

Vero cells were seeded into 96-well microtiter plates at 104 cells per well in 100 μL growth medium (MEM+10% FBS). Individual serum samples were heat-inactivated at 56° C. for 30 min. Two-fold serial dilutions of serum samples in assay medium (MEM+2% FBS) were mixed with equal volumes of an EV71 (vaccine strain) suspension at 2000 units of 50% tissue culture infectious dose (TCID50) per mL and incubated at 37° C. for 1.5 hours. 100 μL of each serum-virus mixture was added to three wells (final virus titer 100 TCID50 per well). Each well was scored for CPE at 5 days post-infection. The end-point neutralizing titer was defined as the highest serum dilution in which at least two of the three replicates were negative for CPE. Seroconversion was defined as a reciprocal neutralizing titer ≥128 [33].

Statistics

Data from animal studies were compiled in Microsoft Excel and analyzed using Excel or Prism 5 (GraphPad, Inc). Student's t-test was used on log-transformed reciprocal neutralizing titers to compare immunogenicity between groups. P values ≤0.05 were considered significant.

Results

Characterization of Purified Inactivated EV71 Material

Western blotting with a monoclonal antibody specific for EV71 VP2 and VP0 proteins confirmed the presence of EV71 antigen in purified inactivated material (samples from a typical batch shown in FIG. 3, left). The estimated purity of EV71, based on image intensity measurements of colloidal blue-stained gels (same samples in FIG. 3, right), was >80% in all batches using this process, typically 85-90%. Typical yields from the process outlined above were approximately 300 μg of protein per liter of harvest.

Electron microscopy revealed a mixture of filled and empty icosahedral capsids (FIG. 4), consistent with the observation of VP0 in Western blotting. A particle concentration estimate performed by mixing the purified inactivated EV71 with a polystyrene bead standard was approximately 3E+10 particles/mL.

Immunogenicity of EV71 Antigen Formulated with or without Aluminum Hydroxide

Immunogenicity in mice of heat-inactivated EV71 antigen (inactivated by heat at 56° C. for 6 hours) was compared to EV71 antigen that was chemically in activated with BEI. The BEI-inactivated EV71 virus exhibited superior immunogenicity, inducing approximately a 6.4-fold higher neutralizing titer at 28 days post-immunization as compared to the heat-inactivated virus. The neutralizing titer with BEI-inactivated virus was approximately 1.5-fold higher than that of the heat-inactivated virus at 56 days post-immunization.

Subsequently, we tested the immunogenicity of BEI-inactivated, purified EV71 preparations in mice at different concentrations with or without adjuvant. The presence of aluminum hydroxide produced higher seroconversion rates at 28 days after the first dose (Table 1 below).

TABLE 1

Seroconversion rates in BALB/c mice immunized with purified inactivated EV71.

| Group | Treatment | Day 28 % seroconverted (n) | Day 42 % seroconverted (n) | Day 56 % seroconverted (n) |
|---|---|---|---|---|
| 1 | PBST[a] control | 0 | 0 | 0 |
| 2 | 0.12 μg EV71 | 12.5 (1/8) | 100 (8/8) | 100 (8/8) |
| 3 | 0.6 μg EV71 | 12.5 (1/8) | 87.5 (7/8) | 100 (8/8) |
| 4 | 3 μg EV71 | 37.5 (3/8) | 100 (8/8) | 100 (8/8) |
| 5 | Alum control | 0 | 0 | 0 |
| 6 | 0.12 μg EV71 + Alum | 37.5 (3/8) | 100 (8/8) | 100 (8/8) |
| 7 | 0.6 μg EV71 + Alum | 100 (8/8) | 100 (8/8) | 100 (8/8) |
| 8 | 3 μg EV71 + Alum | 100 (8/8) | 100 (8/8) | 100 (8/8) |

[a]PBST = Phosphate Buffered Saline + 0.002% (v/v) Tween 80, buffer base for purified inactivated EV71.
Mice were immunized with inactivated virus with or without Alhydrogel at 28, 42 and 56 days post primary immunization. Seroconversion is defined as a neutralizing antibody titre of ≥128.
doi:10.1371/journal.pntd.0002538.t001

Neutralizing antibody titers in groups receiving antigen with adjuvant, compared to groups receiving antigen alone ranged from 11-to-23-fold higher at day 28 (after 1 dose), 4-to 6-fold higher at day 42 (after 2 doses) and 2.4-to 9-fold higher at day 56 (two weeks after 2nd dose) (FIG. 5). The differences were statistically significant at all dose levels (P<0.05). Follow-up to 91 and 120 days showed that high titers were sustained and did not significantly decrease from day 56 (FIG. 5).

Determination of the Optimum Immunogenic Dose

Figure 6:
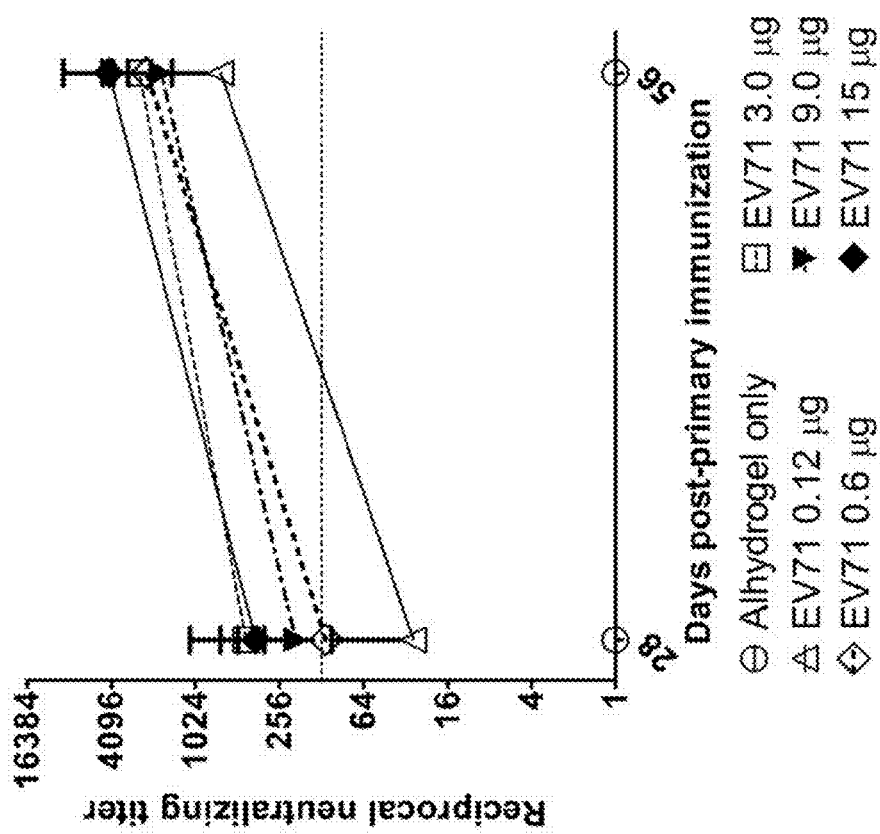
Figure 7:
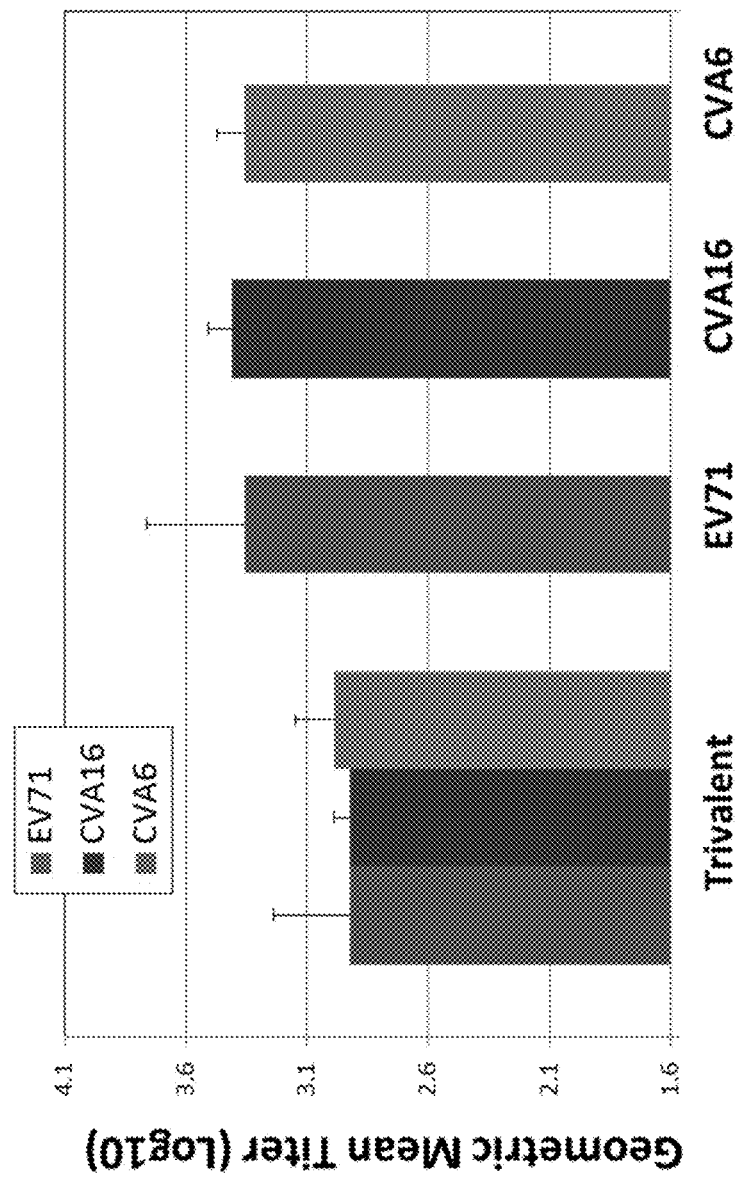
Figure 8:
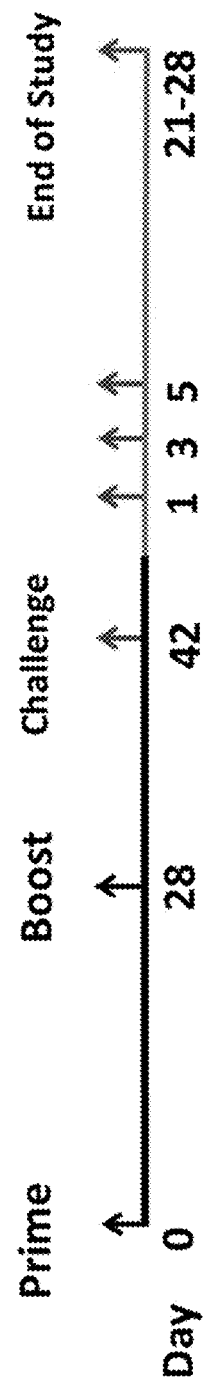
Figure 9:
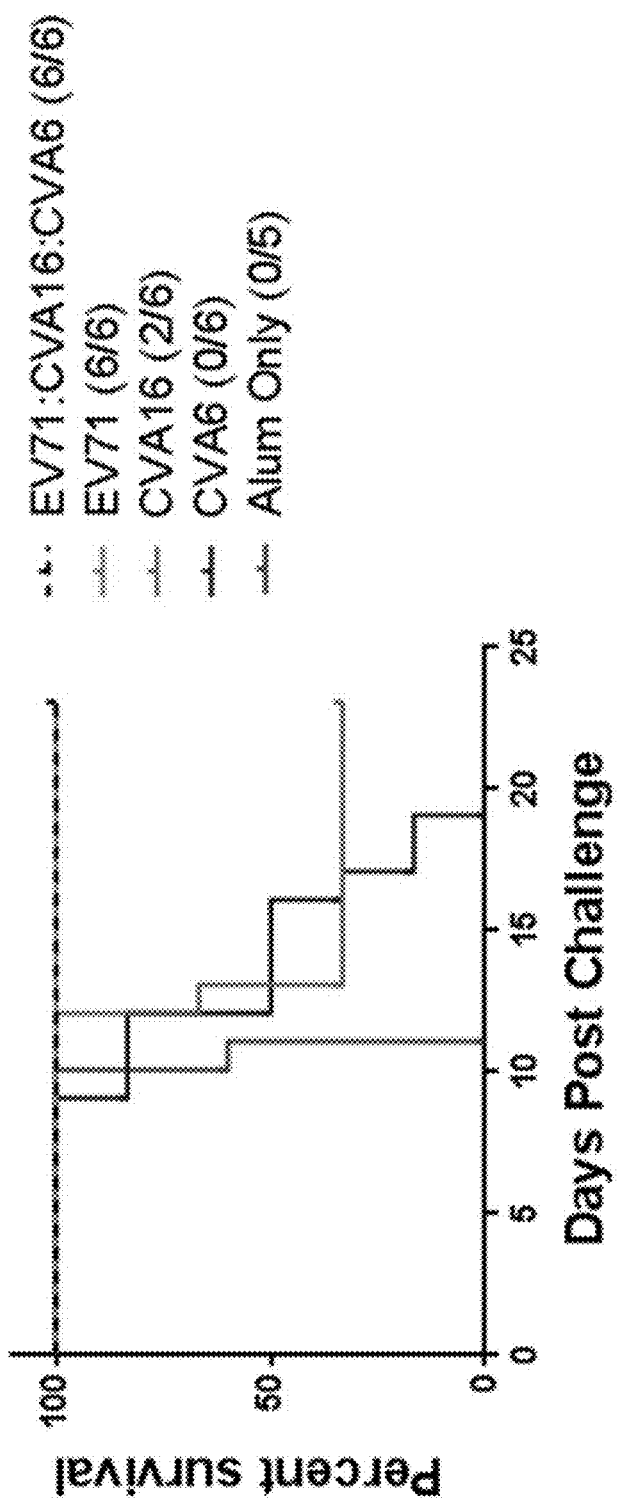
Figure 10:
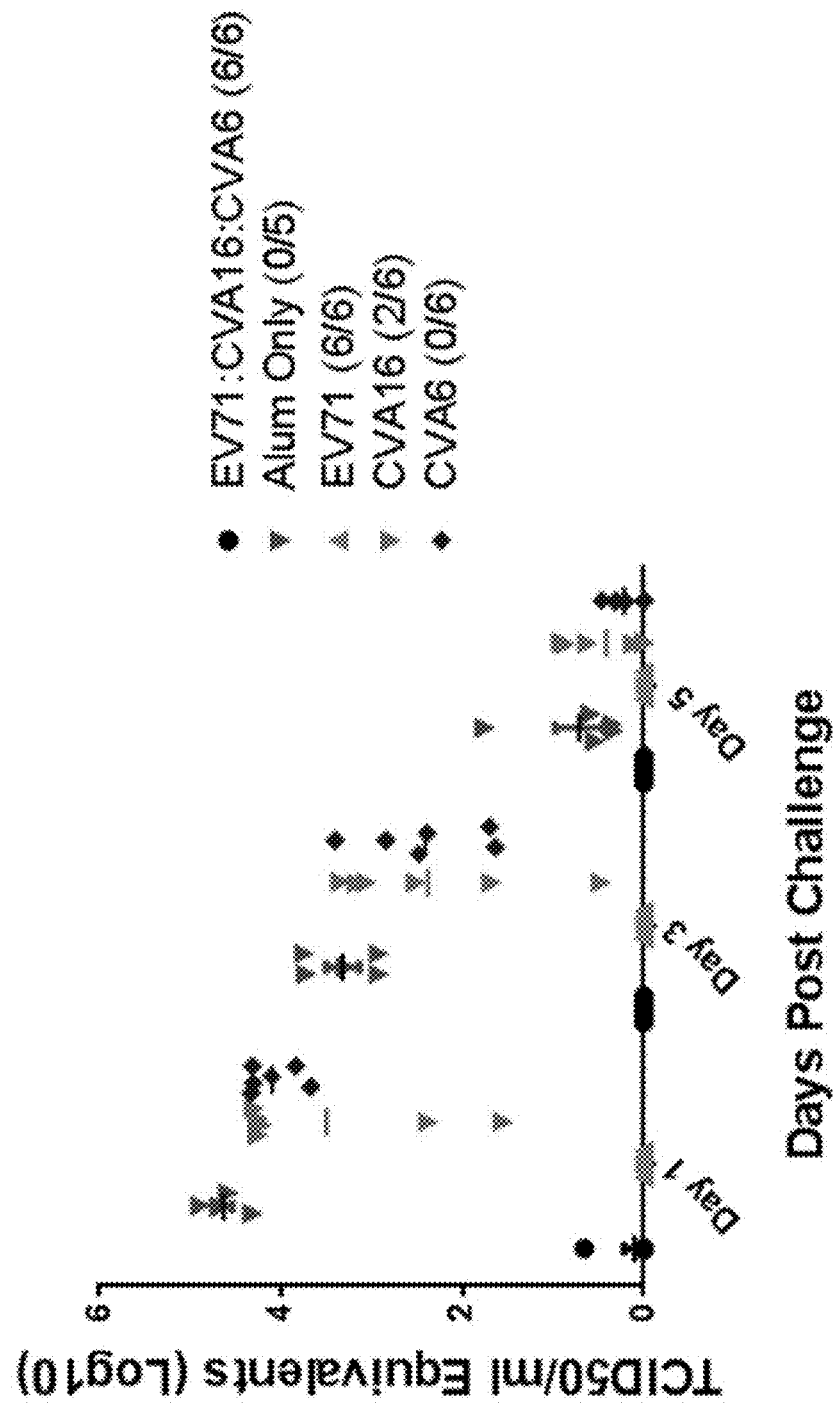
Figure 11:
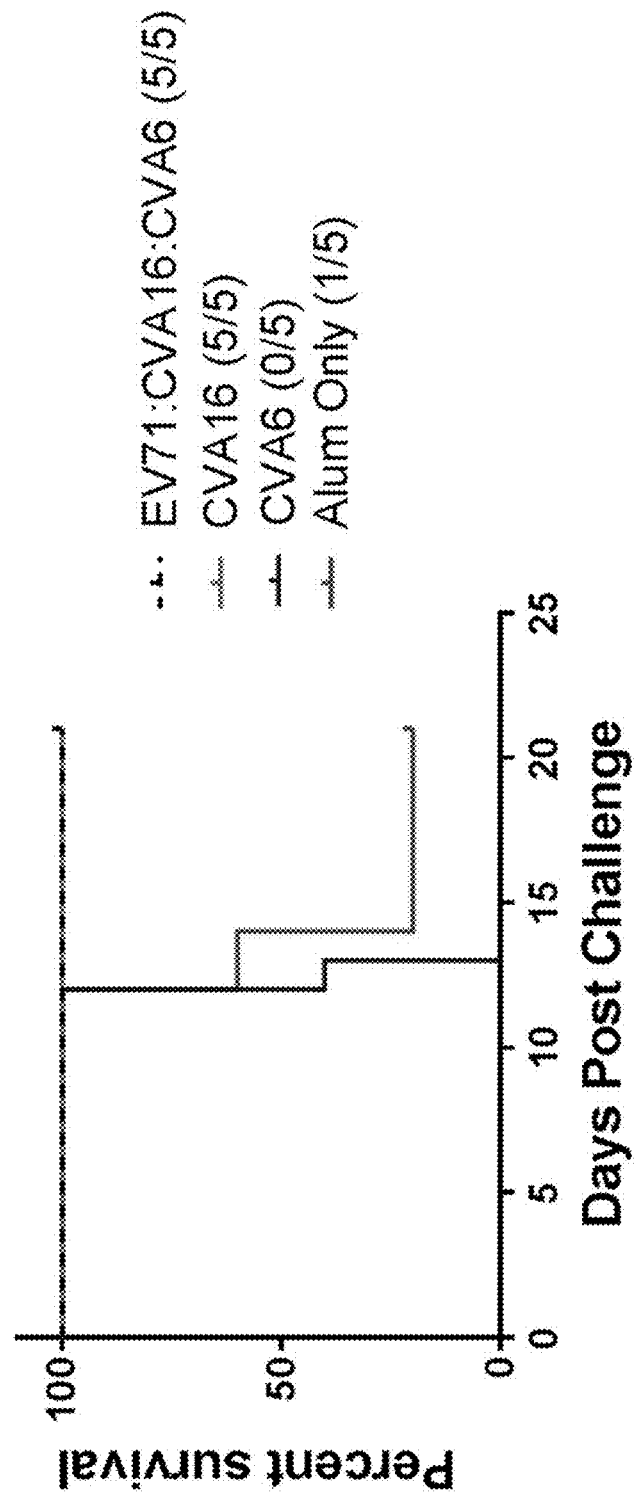

Following a single dose, only the 3 µg and the 15 µg dose levels elicited a high neutralizing antibody response by day 28 (FIG. 6). Seroconversion rates for all groups were incomplete, ranging from 10% to 80% depending on the dose (Table 2 below). However, a booster immunization induced significantly ($P \leq 0.05$) higher levels of neutralizing antibodies in all groups of animals (FIG. 6). Twenty-eight days after the boost, only the lowest dose of 0.12 µg was significantly less immunogenic than the highest dose of 15 µg; doses from 0.6 µg and higher produced equivalent titers. In addition, 100% seroconversion was observed following the booster dose in animals receiving vaccine doses of 3 µg or higher (Table 2 below).

TABLE 2

Seroconversion rates following varying doses of purified inactivated EV71.

| Group | Dose | Day 28 % seroconverted (n) | Day 56 % seroconverted (n) |
|---|---|---|---|
| 1 | Alum control | 0 (0/10) | 0 (0/10) |
| 2 | 0.12 µg EV71 + Alum | 10 (1/10) | 50 (5/10) |
| 3 | 0.6 µg EV71 + Alum | 20 (2/10) | 90 (9/10) |
| 4 | 3 µg EV71 + Alum | 70 (7/10) | 100 (10/10) |
| 5 | 9 µg EV71 + Alum | 40 (4/10) | 100 (10/10) |
| 6 | 15 µg EV71 + Alum | 80 (8/10) | 100 (10/10) |

BALB/c mice were immunized with purified inactivated EV71 virus with Alhydrogel, at 28 days and 56 days post primary immunization. Seroconversion is defined as a neutralizing antibody titre of ≥128.
doi:10.1371/journal.pntd.0002538.t002

Safety of the EV71 Inactivated Vaccine

A toxicological study using this animal model to test low and high dose vaccine formulations was also conducted. The results indicated that no morbidity or mortality occurred in any animals, and no skin reactions (i.e., no erythema or edema) at the site of injection were found in any animals. Hematology and clinical chemistry parameters remained within the normal range for NZW rabbits. Animals in the EV71 vaccine-treated groups exhibited no differences from the control groups in group averages of body mass, body mass change during the study period, or food consumption. At day 30, males treated with Alhydrogel placebo had higher thymus weights compared to the saline placebo group. At day 56, EV71 vaccine-treated females had higher adrenal, ovary/oviduct, and uterus weights compared to the Alhydrogel placebo group. However, no lesions of pathological significance were found on the reproductive or other internal organs.

Muscular degeneration at the site of injection, with or without mononuclear cell/eosinophil infiltration, were observed in a sub-population of animals in all groups receiving formulations containing aluminum hydroxide including the Alhydrogel placebo group, but not in animals which received the saline placebo (Table 3 below). The lesions had healed or were markedly reduced by day 56, i.e., 28 days after the last immunization for the Alhydrogel placebo and low dose groups, and 14 days after the last immunization for the high dose group.

TABLE 3

Muscular lesions at the site of injection in rabbit toxicological study, 2 days after the last immunization.

| | | | Muscle Degeneration (animals/group) | | |
|---|---|---|---|---|---|
| Group | Treatment | Dose of EV71 (µg) | Without Infiltration | With Infiltration | Total[a] |
| G1 | Saline Placebo | 0 | 0/12 | 0/12 | 0/12 |
| G2 | Alhydrogel Placebo[b] | 0 | 4/16 | 2/16 | 6/16 |
| G3 | Vaccine Low Dose | 0.6 | 4/20 | 6/20 | 10/20 |
| G4 | Vaccine High Dose | 3.0 | 0/20 | 8/20 | 8/20 |

[a]Values shown under total are the total number of observations of muscle degeneration with and without MNC/eosinophil infiltration.
[b]The Alhydrogel Placebo group received an Alhydrogel-only adjuvant formulation.
doi:10.1371/journal.pntd.0002538.t003

Discussion

A purified, inactivated, aluminum hydroxide-adjuvanted EV71 vaccine was produced, the immunogenicity of several formulations were evaluated in mice, and the toxicology of the vaccine was evaluated in rabbits. The route of administration, dose levels, dosing schedule, and selection of parameters monitored in this study were designed according to industry standard recommendations for evaluation of vaccine safety [37]. No clinical or hematological abnormalities, or pathological signs on internal organs were found. Injection site lesions were localized, microscopic, and transient, and consistent with aluminum salt-induced lesions reported by other investigators [38].

The purified inactivated EV71 antigen preparation was shown to elicit neutralizing antibody responses to the homologous virus in mice, which were significantly increased by the addition of aluminum hydroxide adjuvant. Analysis of the neutralizing antibody responses induced by the various antigen concentrations established i) the requirement of two doses for optimum immunogenicity and reliable seroconversion, and ii) the selection of low (0.6 µg antigen per dose) and high (3 µg) doses. The neutralizing antibody titers elicited by the inactivated vaccine in animals were over the target titer of 128 and were sustained at high levels for over 3 months after the last immunization. This titer was the minimum protective antibody dose in a neonatal mouse passive immunization-challenge model of EV71 infection [33].

Example 2

Cross-Reactivity of Anti-CVA16 Antibodies Against Other CVA16 Isolates

Serum samples collected on day 42 post-vaccination with inactivated CVA16 were pooled and tested by microneutralization assay. Antibodies raised against CVA16 efficiently neutralized other CVA16 isolates (Table 4).

TABLE 4

Cross-reactivity of anti-CVA16/P-0 antibodies against other CVA16 isolates.

| Virus | Neutralizing titer |
|---|---|
| CVA16 P-0 | ≥5120 |
| CVA16/737 | 2560 |
| CVA16/721 | 2560 |

TABLE 4-continued

Cross-reactivity of anti-CVA16/P-0 antibodies against other CVA16 isolates.

| Virus | Neutralizing titer |
|---|---|
| CVA16/494 | 1280 |
| CVA16/1160 | 2560 |

Example 3

Antigenic Stability of Vero-Adapted Viruses

Figure 13:
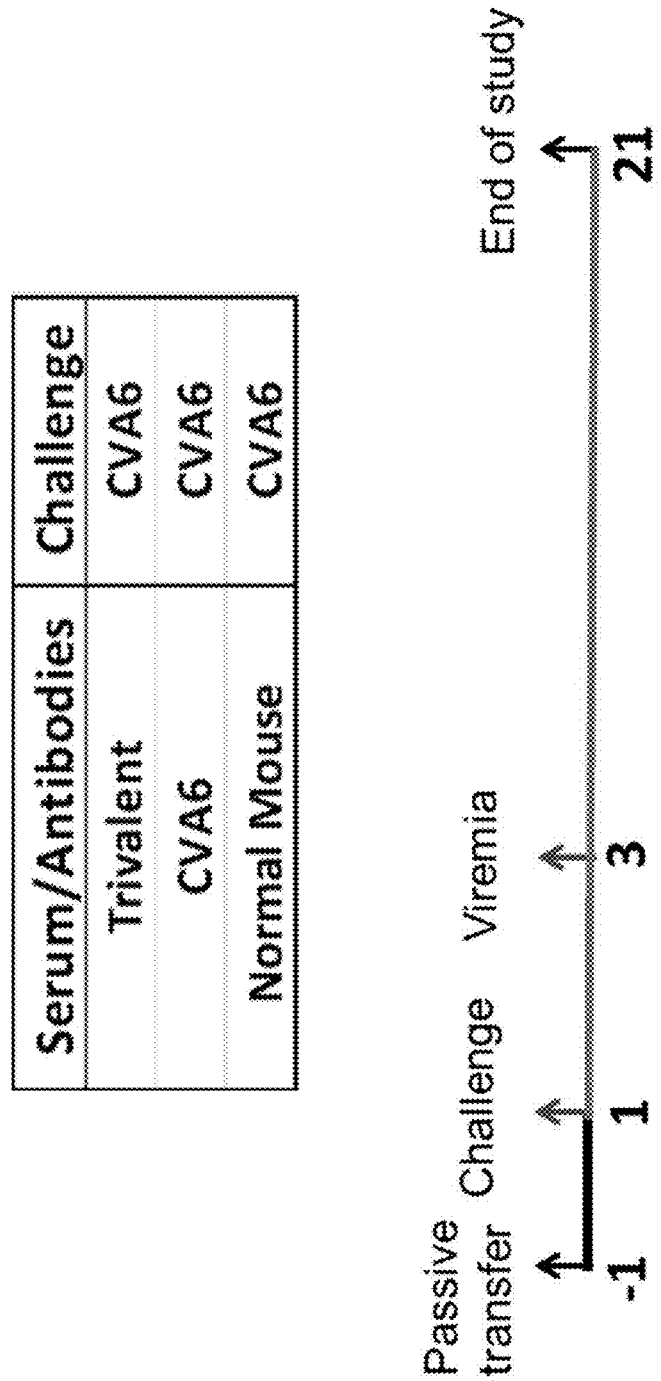

Mice were vaccinated with inactivated CVA16 (P-0) or CVA6 (P-0) along with alum. Serum samples collected after two immunizations (day 0, 28) were pooled and tested for neutralization antibody titers using a conventional TCID50-based assay (Table 5). No significant differences in neutralizing titers were observed between adapted and unadapted viruses, indicating no effect on antigenicity.

TABLE 5

| Antigenic stability of vero-adapted viruses. | |
|---|---|
| Assay virus | Neutralizing titer of pooled antisera |
| CVA16 | |
| CVA16 p0 (RD cell) | 320 |
| CVA16 p3 (Vero) | 320 |
| CVA6 | |
| CVA6 p0 (RD cell) | 2560 |
| CVA6 p11 (Vero) | 1280 |

Example 4

Immunogenicity of Trivalent HFMD Vaccine

The following Example demonstrates the efficacy of an inactivated EV71, CVA6, and CVA16 trivalent HFMD vaccine in adult mice. Both active immunization and passive transfer studies were performed using adult mice.

The inactivated monovalent EV71, CA6, and CA16 vaccines were formulated as described in Examples 1-14. The three monovalent vaccines were combined at a ratio of 1:1:1 to produce the inactivated trivalent vaccine. Each of the inactivated monovalent vaccines were used as controls. Adult A129 (α/β interferon (IFN) receptor deficient) and AG129 (α/β, γ IFN receptor deficient) mice were used for the studies described in this Example.

Cross-Neutralizing Potential of Sera after Immunization with Monovalent Vaccines Groups of AG129 mice were vaccinated with 1.5 μg of the EV71, CVA16, or CVA6 monovalent vaccine on day 0 and day 28. Serum collected on day 42 post-vaccination was pooled per group and tested by microneutralization assay against each virus. The results are depicted in Table 6.

TABLE 6

| | Neutralizing titer | | |
|---|---|---|---|
| Anti-serum | EV71 | CVA16 | CVA6 |
| Anti-EV71 | 2280 | <40 | <40 |
| Anti-CVA16 | <40 | ≥5120 | <40 |
| Anti-CVA6 | <40 | <40 | ≥5120 |

The results in Table 6 indicate that no cross-neutralization was observed between the viruses tested.

Immunogenicity of HFMD Vaccines

AG129 mice were vaccinated either with 1.5 μg of one of the monovalent vaccine or a trivalent mixture of 1.5 μg of each of EV71, CVA6, and CVA16 on day 0 and day 28. Serum samples were collected from mice on day 42. The trivalent immune serum was tested against EV71, CVA16, and CVA6. Each monovalent immune serum was tested against its homologous virus. The geometric mean titer for each vaccine is depicted in FIG. 7.

Vaccine Efficacy Against EV71 and CVA16 in Mouse Model

The efficacy of the trivalent vaccine was then tested in a murine model of EV71 and CVA16 infection. Groups (n=5-6) of four-week old AG129 mice were vaccinated intramuscularly (IM). The monovalent and trivalent vaccines described above were adjuvanted with equal volume of alum (Alhydrogel 85) by mixing on a rotator for 4 hrs at 4° C. as described in Example 2. Mice were vaccinated with a monovalent vaccine at a dosage of 1.5 μg per animal, the trivalent vaccine mixture at a total dosage of 4.5 μg per animal (1.5 μg per animal of each monovalent vaccine), or alum adjuvant as a control. The mice were challenged with virus via intraperitoneal (IP) injection at a challenge dosage of $9.8\times10^5$ $TCID_{50}$/400 μl virus. The treatment and challenge for each mouse group, as well as the schedule of treatment and challenge is depicted in FIG. 8.

As shown in FIG. 9, six out of six mice vaccinated with either the EV71 monovalent vaccine or the trivalent vaccine survived at least 25 days post-challenge with mouse-adapted EV71. However, only two out of six mice vaccinated with the CVA16 vaccine and no mice vaccinated with the CVA6 vaccine survived 20 days post-challenge with EV71, indicating that no cross-protection was observed.

The vaccines were also tested for their ability to inhibit EV71 viremia. Viral titers were measured at days 1, 3, and 5 post-challenge with EV71 (FIG. 10). Serum samples from the vaccinated mice were collected on days 1, 3, and 5 post-challenge with EV71 and viral titer was determined by Real Time RT-PCR using a SYBR Green Kit (Qiagen). A standard curve was generated from serially diluted mouse adapted virus stock. Normal mouse serum was used as a negative control and to determine cut off values. The results indicate that both the EV71 monovalent vaccine and the trivalent vaccine were able to reduce viral titer in serum to approximately zero, as measured by $TCID_{50}$/ml equivalents (FIG. 10).

As shown in FIG. 11, five out of five mice vaccinated with either the CVA16 monovalent vaccine or the trivalent vaccine survived at least 20 days post-challenge with mosue-adapted CVA16. However, no mice vaccinated with the CVA6 vaccine survived 15 days post-challenge with EV71, indicating that no cross-protection was observed.

The vaccines were also tested for their ability to inhibit CVA16 viremia. Viral titers were measured at days 1, 3, and 5 post-challenge with CVA16 (FIG. 12). Serum samples from the vaccinated mice were collected on days 1, 3, and 5 post-challenge with CVA16 and viral titer was determined by Real Time RT-PCR using a SYBR Green Kit (Qiagen). A standard curve was generated from serially diluted mouse adapted virus stock. Normal mouse serum was used as a negative control and to determine cut off values. The results indicate that both the CVA16 monovalent vaccine and the trivalent vaccine were able to reduce viral titer in serum to approximately zero, as measured by $TCID_{50}$/ml equivalents (FIG. 12).

Vaccine Efficacy Against CVA6 Utilizing Passive Transfer

The efficacy of the trivalent vaccine was then tested in a murine model of CVA6 infection. Groups (n=5-6) of three-week old A129 mice were passively immunized via intraperitoneal (IP) injection with neutralizing antibody serum. Neutralizing antibody serum was raised in mice by vaccinating mice with the CVA6 monovalent vaccine at a dosage of 1.5 µg per animal or with the trivalent vaccine mixture at a total dosage of 4.5 µg per animal (1.5 µg per animal of each monovalent vaccine). Serum samples containing neutralizing antibodies were then collected from each group at day 42 post vaccination and pooled per group and tested by microneutralization test. For the trivalent serum, the geometric mean antibody titer for EV71 was 640, the geometric mean antibody titer for CVA16 was 1280, and the geometric mean antibody titer for CVA6 was 1280. For the CVA6 monovalent serum, the geometric mean antibody titer for CVA6 was 5120. The mice were challenged with mouse-adapted CVA6 virus via intraperitoneal (IP) injection at a challenge dosage of $2.31 \times 10^4$ $TCID_{50}/200$ µl CVA6. The passive transfer and challenge for each mouse group, as well as the schedule of treatment and challenge is depicted in FIG. 13.

FIG. 14 depicts the results of passive immunization with the trivalent serum or the CVA6 monovalent serum. Six out of six mice immunized with either the trivalent serum or the CVA6 monovalent serum survived 20 days post-challenge with CVA6, while only one mouse out of six immunized with control serum from normal mouse survived 20 days post-challenge with CVA6 (FIG. 14). The results indicate that passive transfer of serum from mice vaccinated with the trivalent vaccine was protective against homologous viral challenge with CVA6.

The protective sera were also tested for their ability to inhibit CVA6 viremia. Viral titers were measured at days 1, 3, and 5 post-challenge with CVA6 (FIG. 15). Serum samples from the vaccinated mice were collected on days 1, 3, and 5 post-challenge with CVA6 and viral titer was determined by Real Time RT-PCR using a SYBR Green Kit (Qiagen). A standard curve generated from serially diluted mouse adapted virus stock. Normal mouse serum was used as a negative control and to determine cut off values. The results indicate that serum from mice vaccinated with either the CVA6 monovalent vaccine or the trivalent vaccine was able to reduce viral titer in serum to approximately zero, as measured by $TCID_{50}$/ml equivalents (FIG. 25).

CONCLUSIONS

The results demonstrate that antibodies to the HFMD viruses EV71, CVA16, or CVA6 did not cross-neutralize in vitro or cross-protect mice from lethal challenge, and that inactivated preparations of EV71, CVA16, and CVA6 are immunogenic in mice when administered as monovalent or multivalent vaccine formulations. The results also indicate that inactivated preparations of EV71, CVA16, and CVA6 are 100% effective against homologous challenge in the AG129 mouse model for EV71 and CVA16, and in the A129 mouse model for CVA6.

REFERENCES

1. Huang C C, Liu C C, Chang Y C, Chen C Y, Wang S T, et al. (1999) Neurologic complications in children with enterovirus 71 infection. N Engl J Med 341: 936-942.
2. Chang L Y, Huang Y C, Lin T Y (1998) Fulminant neurogenic pulmonary oedema with hand, foot, and mouth disease. Lancet 352: 367-368.
3. Ooi M H, Wong S C, Mohan A, Podin Y, Perera D, et al. (2009) Identification and validation of clinical predictors for the risk of neurological involvement in children with hand, foot, and mouth disease in Sarawak. BMC Infect Dis 9: 3.
4. Solomon T, Lewthwaite P, Perera D, Cardosa M J, McMinn P, et al. (2010) Virology, epidemiology, pathogenesis, and control of enterovirus 71. Lancet Infect Dis 10(11):778-90.
5. McMinn P C (2002) An overview of the evolution of enterovirus 71 and its clinical and public health significance. FEMS Microbiol Rev 26: 91-107.
6. (2012) WPRO Hand, Foot, and Mouth Disease Situation Update, 15 May 2012. Western Pacific Regional Office of the World Health Organization. pp. 4.
7. (2012) Updates on HFMD Situation in Singapore (23 May 2012). Hand, Foot & Mouth Disease: Updates: Singapore Ministry of Health.
8. Pallansch M A, Roos R (2007) Enteroviruses: polioviruses, coxsackieviruses, and newer enteroviruses. In: Knipe D M, Howley P M, Griffin D E, editors. Fields Virology. Philadelphia, Pa. Lippincott Williams & Wilkins. pp. 839-894.
9. Nagata N, Shimizu H, Ami Y, Tano Y, Harashima A, et al. (2002) Pyramidal and extrapyramidal involvement in experimental infection of cynomolgus monkeys with enterovirus 71. J Med Virol 67: 207-216.
10. Yamayoshi S, Yamashita Y, Li J, Hanagata N, Minowa T, et al. (2009) Scavenger receptor B2 is a cellular receptor for enterovirus 71. Nat Med 15:798-801.
11. Nishimura Y, Shimojima M, Tano Y, Miyamura T, Wakita T, et al. (2009) Human P-selectin glycoprotein ligand-1 is a functional receptor for enterovirus 71. Nat Med 15: 794-797.
12. Oberste M S, Maher K, Kilpatrick D R, Flemister M R, Brown B A, et al. (1999) Typing of human enteroviruses by partial sequencing of VP1. J Clin Microbiol 37: 1288-1293.
13. Lee M S, Tseng F C, Wang J R, Chi C Y, Chong P, et al. (2012) Challenges to licensure of enterovirus 71 vaccines. PLoS Negl Trop Dis 6: e1737.
14. Brown B A, Oberste M S, Alexander J P, Jr., Kennett M L, Pallansch M A (1999) Molecular epidemiology and evolution of enterovirus 71 strains isolated from 1970 to 1998. J Virol 73: 9969-9975.
15. Chan Y F, Sam I C, Abubakar S (2009) Phylogenetic designation of enterovirus 71 genotypes and subgenotypes using complete genome sequences. Infect Genet Evol 10(3):404-12.
16. Yoke-Fun C, AbuBakar S (2006) Phylogenetic evidence for inter-typic recombination in the emergence of human enterovirus 71 subgenotypes. BMC Microbiol 6: 74.
17. Wang S M, Liu C C, Tseng H W, Wang J R, Huang C C, et al. (1999) Clinical spectrum of enterovirus 71 infection in children in southern Taiwan, with an emphasis on neurological complications. Clin Infect Dis 29: 184-190.
18. Ong K C, Devi S, Cardosa M J, Wong K T (2010) Formaldehyde-inactivated whole virus vaccine protects a murine model of Enterovirus 71 encephalomyelitis against disease. J Virol 84: 661-665.
19. Chong P, Hsieh S Y, Liu C C, Chou A H, Chang J Y, et al. (2012) Production of EV71 vaccine candidates. Hum Vaccin Immunother 8: 1775-83.
20. Chen H F, Chang M H, Chiang B L, Jeng S T (2006) Oral immunization of mice using transgenic tomato fruit expressing VP1 protein from enterovirus 71. Vaccine 24: 2944-2951.
21. Meng T, Kolpe A B, Kiener T K, Chow V T, Kwang J (2011) Display of VP1 on the surface of baculovirus and its immunogenicity against heterologous human enterovirus 71 strains in mice. PLoS ONE 6: e21757.
22. Liu J N, Wang W, Duo J Y, Hao Y, Ma C M, et al. (2010) Combined peptides of human enterovirus 71 protect against virus infection in mice. Vaccine 28: 7444-7451.
23. Chiu C H, Chu C, He C C, Lin T Y (2006) Protection of neonatal mice from lethal enterovirus 71 infection by maternal immunization with attenuated *Salmonella enterica* serovar *Typhimurium* expressing VP1 of enterovirus 71. Microbes Infect 8: 1671-1678.
24. Tung W S, Bakar S A, Sekawi Z, Rosli R (2007) DNA vaccine constructs against enterovirus 71 elicit immune response in mice. Genet Vaccines Ther 5: 6.
25. Chung Y C, Ho M S, Wu J C, Chen W J, Huang J H, et al. (2008) Immunization with virus-like particles of enterovirus 71 elicits potent immune responses and protects mice against lethal challenge. Vaccine 26: 1855-1862.
26. Arita M, Nagata N, Iwata N, Ami Y, Suzaki Y, et al. (2007) An attenuated strain of enterovirus 71 belonging to genotype a showed a broad spectrum of antigenicity with attenuated neurovirulence in cynomolgus monkeys. J Virol 81:9386-9395.
27. Mao Q, Dong C, Li X, Gao Q, Guo Z, et al. (2012) Comparative analysis of the immunogenicity and protective effects of inactivated EV71 vaccines in mice. PLoS ONE 7: e46043.
28. Chou A H, Liu C C, Chang J Y, Lien S P, Guo M S, et al. (2012) Immunological Evaluation and Comparison of Different EV71 Vaccine Candidates. Clin Dev Immunol 2012: 831282.
29. Li Y P, Liang Z L, Gao Q, Huang L R, Mao Q Y, et al. (2012) Safety and immunogenicity of a novel human Enterovirus 71 (EV71) vaccine: a randomized, placebo-controlled, double-blind, Phase I clinical trial. Vaccine 30: 3295-3303.
30. Zhu F C, Meng F Y, Li J X, Li X L, Mao Q Y, et al. (2013) Efficacy, safety, and immunology of an inactivated alum-adjuvant enterovirus 71 vaccine in children in China: a multicentre, randomised, double-blind, placebo-controlled, phase 3 trial. Lancet 381: 2024-2032.
31. Cheng A, Fung C P, Liu C C, Lin Y T, Tsai H Y, et al. (2013) A Phase I, randomized, open-label study to evaluate the safety and immunogenicity of an enterovirus 71 vaccine. Vaccine 31: 2471-2476.
32. Bahnemann H G (1990) Inactivation of viral antigens for vaccine preparation with particular reference to the application of binary ethylenimine. Vaccine 8: 299-303.
33. Yu C K, Chen C C, Chen C L, Wang J R, Liu C C, et al. (2000) Neutralizing antibody provided protection against enterovirus type 71 lethal challenge in neonatal mice. J Biomed Sci 7: 523-528.
34. Liu C C, Guo M S, Lin F H, Hsiao K N, Chang K H, et al. (2011) Purification and characterization of enterovirus 71 viral particles produced from vero cells grown in a serum-free microcarrier bioreactor system. PLoS One 6: e20005.
35. Shingler K L, Yoder J L, Carnegie M S, Ashley R E, Makhov A M, et al. (2013) The Enterovirus 71 A-particle Forms a Gateway to Allow Genome Release: A CryoEM Study of Picornavirus Uncoating. PLoS Pathog 9: e1003240.
36. Curry S, Chow M, Hogle J M (1996) The poliovirus 135S particle is infectious. J Virol 70: 7125-7131.
37. Verdier F (2002) Non-clinical vaccine safety assessment. Toxicology 174: 37-43.
38. Verdier F, Burnett R, Michelet-Habchi C, Moretto P, Fievet-Groyne F, et al. (2005) Aluminium assay and evaluation of the local reaction at several time points after intramuscular administration of aluminium containing vaccines in the Cynomolgus monkey. Vaccine 23: 1359-1367.
39. Wang Y F, Chou C T, Lei H Y, Liu C C, Wang S M, et al. (2004) A mouseadapted enterovirus 71 strain causes neurological disease in mice after oral infection. J Virol 78: 7916-7924.
40. Wang W, Duo J, Liu J, Ma C, Zhang L, et al. (2011) A mouse muscle-adapted enterovirus 71 strain with increased virulence in mice. Microbes Infect 13: 862-870.
41. Huang S W, Wang Y F, Yu C K, Su I J, Wang J R (2012) Mutations in VP2 and VP1 capsid proteins increase infectivity and mouse lethality of enterovirus 71 by virus binding and RNA accumulation enhancement. Virology 422: 132-143.
42. Khong W X, Yan B, Yeo H, Tan E L, Lee J J, et al. (2011) A non mouse-adapted Enterovirus 71 (EV71) strain exhibits neurotropism causing neurological manifestations in a novel mouse model of EV71 infection. J Virol 86(4):2121-31.
43. Caine E A, Partidos C D, Santangelo J D, Osorio J E (2013) Adaptation of enterovirus 71 to adult interferon deficient mice. PLoS ONE 8: e59501.
44. Huang M L, Chiang P S, Chia M Y, Luo S T, Chang L Y, et al. (2013) Crossreactive neutralizing antibody responses to enterovirus 71 infections in young children: implications for vaccine development. PLoS Negl Trop Dis 7: e2067.
45. Chen Y, Li C, He D, Cheng T, Ge S, et al. (2013) Antigenic analysis of divergent genotypes human Enterovirus 71 viruses by a panel of neutralizing monoclonal antibodies: current genotyping of EV71 does not reflect their antigenicity. Vaccine 31: 425-430.
46. Kung S H, Wang S F, Huang C W, Hsu C C, Liu H F, et al. (2007) Genetic and antigenic analyses of enterovirus 71 isolates in Taiwan during 1998-2005. Clin Microbiol Infect 13: 782-787.
47. Mizuta K, Aoki Y, Suto A, Ootani K, Katsushima N, et al. (2009) Crossantigenicity among EV71 strains from different genogroups isolated in Yamagata, Japan, between 1990 and 2007. Vaccine 27: 3153-3158.
48. Lee B Y, Wateska A R, Bailey R R, Tai J H, Bacon K M, et al. (2010) Forecasting the economic value of an Enterovirus 71 (EV71) vaccine. Vaccine 28: 7731-7736.

The invention claimed is:

1. A hand, foot, and mouth immunogenic composition comprising at least one virus that causes hand, foot and mouth disease in humans and a detergent in an effective concentration, wherein:
   a. the at least one virus is an intact, inactivated virus;
   b. the composition does not comprise an adjuvant, or comprises an aluminum salt adjuvant; or
   c. (a) and (b).

2. The immunogenic composition of claim 1, wherein the detergent comprises polysorbate, and wherein the effective concentration ranges from about 0.001% to about 0.01%.

3. The immunogenic composition of claim 1, wherein the at least one intact, inactivated virus was chemically inactivated with one or more of:
   a. beta-propiolactone (BPL);
   b. formalin;
   c. binary ethylenimine (BEI);
   d. binary ethylenimine (BEI), wherein the at least one intact, inactivated virus inactivated by BEI comprises one or more modifications;
   e. binary ethylenimine (BEI), wherein the at least one intact, inactivated virus inactivated by BEI comprises one or more modifications, wherein the one or more modifications comprise a modified nucleic acid; or
   f. binary ethylenimine (BEI), wherein unreacted BEI was hydrolyzed with sodium thiosulfate.

4. The immunogenic composition of claim 1, wherein:
   a. the aluminum salt adjuvant is selected from the group consisting of alum, aluminum phosphate, aluminum hydroxide, potassium aluminum sulfate, and Alhydrogel 85; or
   b. the aluminum salt adjuvant is selected from the group consisting of alum, aluminum phosphate, aluminum hydroxide, potassium aluminum sulfate, and Alhydrogel 85, and wherein at least 75%, at least 80%, at least 85%, at least 90%, at 95%, at least 97%, at least 99%, or 100% of the antigen is adsorbed to the adjuvant.

5. A hand, foot, and mouth immunogenic composition comprising at least one intact, inactivated virus that causes hand, foot and mouth disease in humans and a detergent in an effective concentration, wherein:
   a. the at least one intact, inactivated virus was inactivated with BEI;
   b. the composition does not comprise an adjuvant, or comprises an aluminum salt adjuvant; or
   c. (a) and (b).

6. The immunogenic composition of claim 5, wherein the at least one intact, inactivated virus inactivated by BEI comprises one or more modifications, and wherein the one or more modifications comprise a modified nucleic acid.

7. The immunogenic composition of claim 5, wherein unreacted BEI was hydrolyzed with sodium thiosulfate.

8. The immunogenic composition of claim 5, wherein the detergent comprises polysorbate, and wherein the effective concentration is from about 0.001% to about 0.01%.

9. The immunogenic composition of claim 5, wherein the at least one intact, inactivated virus is EV71.

10. The immunogenic composition of claim 5, wherein the at least one intact, inactivated virus comprises one or more antigens selected from EV71.

11. The immunogenic composition of claim 10, wherein the one or more antigens comprise at least one non-human cell adaptation mutation.

12. The immunogenic composition of claim 11, wherein the one or more antigens comprise:
   a. the VP1 polypeptide of EV71, and wherein the VP1 polypeptide comprises the at least one non-human cell adaptation mutation;
   b. the 5' untranslated region (UTR) of EV71, and wherein the 5' UTR of EV71 comprises the at least one non-human cell adaptation mutation; or
   c. the VP1 polypeptide of EV71, and wherein the VP1 polypeptide comprises the at least one non-human cell adaptation mutation and the 5' untranslated region (UTR) of EV71, and the 5' UTR of EV71 comprises the at least one non-human cell adaptation mutation.

13. The immunogenic composition of claim 11, wherein the non-human cell is a Vero cell line.

14. The immunogenic composition of claim 1, wherein:
   a. the aluminum salt adjuvant is selected from the group consisting of alum, aluminum phosphate, aluminum hydroxide, potassium aluminum sulfate, and Alhydrogel 85; or
   b. the aluminum salt adjuvant is selected from the group consisting of alum, aluminum phosphate, aluminum hydroxide, potassium aluminum sulfate, and Alhydrogel 85, and wherein at least 75%, at least 80%, at least 85%, at least 90%, at 95%, at least 97%, at least 99%, or 100% of the antigen is adsorbed to the adjuvant.

15. A method for inducing an immune response in a subject in need thereof, comprising administering to the subject a therapeutically effective amount of the immunogenic composition of claim 5.

16. The method of claim 15, wherein the administering induces a protective immune response in the subject, and wherein:
   a. the immune response comprises an immune response against EV71; or
   b. the immune response comprises an immune response against one or more EV71 viral genotypes selected from B2, B4, B5, C2, and C4.

17. The method of claim 15, wherein the administering is selected from the group consisting of subcutaneous delivery, transcutaneous delivery, intradermal delivery, subdermal delivery, intramuscular delivery, peroral delivery, oral delivery, intranasal delivery, buccal delivery, sublingual delivery, intraperitoneal delivery, intravaginal delivery, anal delivery and intracranial delivery.

18. A method for inactivating a hand, foot, and mouth virus preparation, comprising:
   (a) isolating the hand, foot, and mouth virus preparation from one or more non-human cells, wherein the cells are used to produce the virus preparation; and
   (b) treating the virus preparation with an effective amount of BEI; and
   wherein the virus is EV71.

19. The method of claim 18, wherein:
   a. the virus preparation is treated with BEI in an amount that ranges from about 0.25% v/v to about 3.0% v/v;
   b. the virus preparation is treated with BEI at a temperature that ranges from about 25° C. to about 42° C.;
   c. the virus preparation is treated with BEI for a period of time that ranges from about 1 hour to about 10 hours; or
   d. any combination of (a) to (c) above.

20. The method of claim 19, wherein the method further comprises hydrolyzing unreacted BEI with an effective amount of sodium thiosulfate, and wherein the effective amount of sodium thiosulfate ranges from about 25 mM to about 100 mM.

* * * * *